United States Patent
Haviv et al.

(10) Patent No.: US 7,592,466 B2
(45) Date of Patent: Sep. 22, 2009

(54) UREAS HAVING ANTIANGIOGENIC ACTIVITY

(75) Inventors: Fortuna Haviv, Deerfield, IL (US); Michael F. Bradley, Covington, WA (US); Daryl R. Sauer, Trevor, WI (US)

(73) Assignee: Abbott Laboratories, Abbott Park, IL (US)

( * ) Notice: Subject to any disclaimer, the term of this patent is extended or adjusted under 35 U.S.C. 154(b) by 1162 days.

(21) Appl. No.: 10/961,362

(22) Filed: Oct. 8, 2004

(65) Prior Publication Data

US 2006/0160806 A1 Jul. 20, 2006

Related U.S. Application Data

(60) Provisional application No. 60/509,949, filed on Oct. 9, 2003.

(51) Int. Cl.
*C07D 295/00* (2006.01)
*C07D 207/00* (2006.01)

(52) U.S. Cl. ........................ 548/538; 548/518
(58) Field of Classification Search .................. 548/518, 548/538
See application file for complete search history.

(56) References Cited

U.S. PATENT DOCUMENTS

| 4,857,527 | A | 8/1989 | Takaya et al. |
|---|---|---|---|
| 2002/0137770 | A1 | 9/2002 | Nara et al. |
| 2003/0195195 | A1 | 10/2003 | Haviv et al. |

FOREIGN PATENT DOCUMENTS

| EP | 1 044 967 | 10/2000 |
|---|---|---|
| WO | 98/00134 | 1/1998 |
| WO | 99/61406 | 12/1999 |
| WO | 01/32621 | 5/2001 |
| WO | 01/55114 | 8/2001 |
| WO | 01/55115 | 8/2001 |
| WO | 01/58899 | 8/2001 |
| WO | 02/08190 | 1/2002 |
| WO | 02/12242 | 2/2002 |
| WO | 02/18368 | 3/2002 |
| WO | 02/094203 | 11/2002 |
| WO | 03/020719 | 3/2003 |
| WO | 03/043983 | 5/2003 |
| WO | 03/068229 | 8/2003 |

OTHER PUBLICATIONS

Schmitz et al. Arch.Pharm. 308(5):359-364 (1975).*
Folkman et al., Cancer Res. 46:467-473 (1986).
Folkman et al., J. Natl. Cancer Inst. 82:4-6 (1989).
Sattler et al., "Core-alkylated and isomeric nicethamide derivatives," Arch. Pharm., 309(76):222-228.
Sattler et al., "On the effect of partially cyclic and core-methylated nicethamide analogues," Arzeim.-Forsch./Drug Res. 27(1):137-141 (1977).
Schmitz et al., "Synthese von Analogen des 6-Methyl-nicethamids," Arch. Pharm. 308(5):359-364 (1975).
Tolsma et al., "Peptides derived from two separate domains of the matrix protein thrombospondin-1 have anti-angiogenic activity," Journal of Cell Biology 122(2):497-511 (1993).
Weidner et al., N. Engl. J. Med. 324(1):1-8 (1991).
Patent Abstract of Japan, 2002069057.

* cited by examiner

*Primary Examiner*—D. Margaret Seaman
*Assistant Examiner*—Nizal S Chandrakumar
(74) *Attorney, Agent, or Firm*—Gregory W. Steele

(57) ABSTRACT

Compounds having the formula

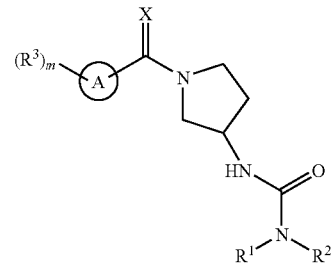

are angiogenesis inhibitors. Also disclosed are compositions containing the compounds, methods of making the compounds, and methods of treatment using the compounds.

6 Claims, No Drawings

UREAS HAVING ANTIANGIOGENIC ACTIVITY

This application claims priority from U.S. Provisional Patent Application Ser. No. 60/509,949, filed Oct. 9, 2003, incorporated herein by reference.

TECHNICAL FIELD

The present invention relates to novel compounds having activity useful for treating conditions which arise from or are exacerbated by angiogenesis, pharmaceutical compositions comprising the compounds, methods of treatment using the compounds, methods of inhibiting angiogenesis, and methods of treating cancer.

BACKGROUND OF THE INVENTION

Angiogenesis is the fundamental process by which new blood vessels are formed and is essential to a variety of normal body activities (such as reproduction, development and wound repair). Although the process is not completely understood, it is believed to involve a complex interplay of molecules which both stimulate and inhibit the growth of endothelial cells, the primary cells of the capillary blood vessels. Under normal conditions these molecules appear to maintain the microvasculature in a quiescent state (i.e., one of no capillary growth) for prolonged periods that may last for weeks, or in some cases, decades. However, when necessary, such as during wound repair, these same cells can undergo rapid proliferation and turnover within as little as five days.

Although angiogenesis is a highly regulated process under normal conditions, many diseases (characterized as "angiogenic diseases") are driven by persistent unregulated angiogenesis. Otherwise stated, unregulated angiogenesis may either cause a particular disease directly or exacerbate an existing pathological condition. For example, the growth and metastasis of solid tumors have been shown to be angiogenesis-dependent. Based on these findings, there is a continuing need for compounds which demonstrate antiangiogenic activity due to their potential use in the treatment of various diseases such as cancer.

SUMMARY OF THE INVENTION

In its principle embodiment the present invention provides a compound of formula (I)

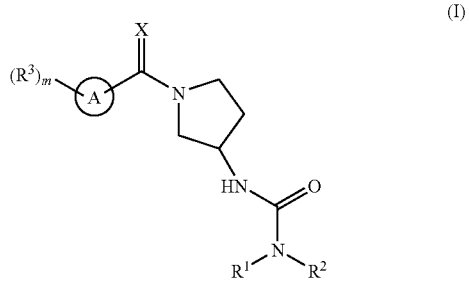

(I)

or a therapeutically acceptable salt thereof, wherein

A is selected from the group consisting of pyridazinyl, pyridinyl, pyridine N-oxide, pyrimidinyl, indol-3-yl, pyrazol-4-yl, pyrazinyl, isoxazol-4-yl, and triazinyl;

$R^1$ and $R^2$ are independently selected from the group consisting of hydrogen, alkenyl, alkoxy, alkoxyalkyl, alkyl, alkynyl, aryl, arylalkyl, cyanoalkyl, cycloalkyl, (cycloalkyl)alkyl, haloalkyl, heterocyclyl, heterocyclylalkyl, hydroxyalkyl, $(NR^A R^B)$alkyl, and $(NR^A R^B)$carbonyl; or $R^1$ and $R^2$, together with the nitrogen atom to which they are attached, form a five- to seven-membered ring containing zero or one additional heteroatom selected from the group consisting of nitrogen, oxygen, and sulfur, wherein the remaining atoms are carbon; wherein the ring can be optionally substituted with one, two, three, or four substituents independently selected from the group consisting of alkoxy, alkoxyalkyl, alkoxycarbonyl, alkoxycarbonylalkyl, alkyl, alkylene, alkylcarbonyl, alkylsulfanylalkyl, aryl, arylalkyl, arylcarbonyl, arylcarbonylalkyl, cycloalkyl, (cycloalkyl)alkyl, (cycloalkyl)carbonyl, (cycloalkyl)carbonylalkyl, ethylenedioxy, haloalkoxy, haloalkyl, heterocyclyl, heterocyclylalkyl, heterocyclylcarbonyl, heterocyclylcarbonylalkyl, hydroxy, hydroxyalkyl, $NR^A R^B$, $(NR^A R^B)$alkyl, and $(NR^A R^B)$carbonyl;

$R^3$ at each occurrence is independently selected from the group consisting of alkenyl, alkoxy, alkoxyalkyl, alkoxycarbonyl, alkyl, alkylcarbonyl, alkylsulfanyl, aryl, arylalkyl, aryloxy, cyano, cyanoalkyl, cycloalkyl, (cycloalkyl)alkyl, halo, haloalkyl, heterocycle, hydroxy, hydroxyalkyl, and nitro;

X is selected from the group consisting of O and S;

m is 0-4; and $R^A$ and $R^B$ are independently selected from the group consisting of hydrogen, alkenyl, alkoxyalkyl, alkyl, alkynyl, alkylcarbonyl, aryl, arylalkyl, cycloalkyl, (cycloalkyl)alkyl, heterocyclyl, heterocyclylalkyl, and hydroxyalkyl. In another embodiment the present invention provides a compound of formula (I) wherein A is pyridinyl; and m, X, $R^1$, $R^2$, and $R^3$ are as defined in formula (I).

In another embodiment the present invention provides a compound of formula (I) wherein X is O; and m, A, X, $R^1$, $R^2$, and $R^3$ are as defined in formula (I).

In another embodiment the present invention provides a compound of formula (I) wherein A is pyridinyl; X is O; $R^3$ is alkyl; m is 1; and $R^1$, $R^2$, and $R^3$ are as defined in formula (I).

In another embodiment the present invention provides a compound of formula (I) wherein A is pyridinyl; X is O; $R^3$ is alkyl; m is 1; $R^1$ is selected from the group consisting of hydrogen and alkyl; and $R^2$ is selected from the group consisting of alkyl and $(NR^A R^B)$alkyl; and $R^A$ and $R^B$ are as defined in formula (I).

In another embodiment the present invention provides a compound of formula (I) wherein A is pyridinyl; X is O; $R^3$ is alkyl; m is 1; $R^1$ is selected from the group consisting of hydrogen and alkyl; and $R^2$ is selected from the group consisting of alkyl and $(NR^A R^B)$alkyl; and $R^A$ and $R^B$ are independently selected from the group consisting of hydrogen and alkyl.

In another embodiment the present invention provides a compound of formula (I) wherein A is pyridinyl; X is O; $R^3$ is alkyl; m is 1; $R^1$ is selected from the group consisting of hydrogen, alkyl, arylalkyl, and hydroxyalkyl; and $R^2$ is arylalkyl.

In another embodiment the present invention provides a compound of formula (I) wherein A is pyridinyl; X is O; $R^3$ is alkyl; m is 1; $R^1$ is selected from the group consisting of hydrogen and alkyl; and $R^2$ is heterocyclylalkyl.

In another embodiment the present invention provides a compound of formula (I) wherein A is pyridinyl; X is O; $R^3$ is alkyl; m is 1; $R^1$ is selected from the group consisting of hydrogen, alkyl, and alkoxyalkyl; and $R^2$ is selected from the group consisting of alkoxyalkyl and alkynyl.

In another embodiment the present invention provides a compound of formula (I) wherein A is pyridinyl; X is O; $R^3$ is alkyl; m is 1; $R^1$ is selected from the group consisting of hydrogen, alkyl, and cyanoalkyl; and $R^2$ is selected from the group consisting of cycloalkyl and (cycloalkyl)alkyl.

In another embodiment the present invention provides a compound of formula (I) wherein A is pyridinyl; X is O; $R^3$ is alkyl; m is 1; $R^1$ is selected from the group consisting of hydrogen and alkyl; and $R^2$ is selected from the group consisting of cyanoalkyl, haloalkyl, and hydroxyalkyl.

In another embodiment the present invention provides a compound of formula (I) wherein A is pyridinyl; X is O; $R^3$ is alkyl; m is 1; and $R^1$ and $R^2$, together with the nitrogen atom to which they are attached, form a five-membered ring containing zero additional heteroatoms wherein the remaining atoms are carbon wherein the ring is optionally substituted with one or two substituents selected from the group consisting of alkylene and alkyl.

In another embodiment the present invention provides a compound of formula (I) wherein A is pyridinyl; X is O; $R^3$ is alkyl; m is 1; and $R^1$ and $R^2$, together with the nitrogen atom to which they are attached, form a six-membered ring containing one additional oxygen atom wherein the remaining atoms are carbon wherein the ring is optionally substituted with one substituent selected from the group consisting of alkoxyalkyl, alkyl, ethylenedioxy, heterocyclyl, hydroxy, and $(NR^A R^B)$carbonyl.

In another embodiment the present invention provides a compound of formula (I) wherein A is pyridinyl; X is O; $R^3$ is alkyl; m is 1; and $R^1$ and $R^2$, together with the nitrogen atom to which they are attached, form a six-membered ring containing one additional nitrogen atom wherein the remaining atoms are carbon wherein the ring is optionally substituted with one or two alkyl substituents.

In another embodiment the present invention provides a compound of formula (I) wherein A is pyridinyl; X is O; $R^3$ is alkyl; m is 1; and $R^1$ and $R^2$, together with the nitrogen atom to which they are attached, form a six-membered ring containing one additional nitrogen atom wherein the remaining atoms are carbon wherein the ring is optionally substituted with one substituent selected from the group consisting of alkoxyalkyl, alkoxycarbonylalkyl, alkyl, aryl, arylalkyl, cycloalkyl, cycloalkylcarbonyl, heterocyclyl, heterocyclylalkyl, and heterocyclylcarbonylalkyl.

In another embodiment the present invention provides a compound of formula (I) wherein A is pyridinyl; X is O; $R^3$ is alkyl; m is 1; and $R^1$ and $R^2$, together with the nitrogen atom to which they are attached, form a seven-membered ring containing zero additional heteroatoms wherein the remaining atoms are carbon.

In another embodiment the present invention provides a compound of formula (I) wherein A is pyridinyl; X is O; $R^3$ is alkyl; m is 1; and $R^1$ and $R^2$, together with the nitrogen atom to which they are attached, form a seven-membered ring containing one additional nitrogen atom wherein the remaining atoms are carbon wherein the ring is optionally substituted with one alkyl substituent.

In another embodiment the present invention provides a compound of formula (I) wherein A is pyridinyl; X is O; $R^3$ is independently selected from the group consisting of alkyl and halo; m is 2; and $R^1$ and $R^2$ are as defined in formula (I).

In another embodiment the present invention provides a compound of formula (I) wherein A is pyridinyl; X is O; $R^3$ is independently selected from the group consisting of alkyl and halo; m is 2; $R^1$ is selected from the group consisting of hydrogen and alkyl; and $R^2$ is selected from the group consisting of alkoxyalkyl, alkyl, and alkylsulfanylalkyl.

In another embodiment the present invention provides a compound of formula (I) wherein A is pyridinyl; X is O; $R^3$ is independently selected from the group consisting of alkyl and halo; m is 2; $R^1$ is selected from the group consisting of hydrogen, alkyl, and arylalkyl; and $R^2$ is arylalkyl.

In another embodiment the present invention provides a compound of formula (I) wherein A is pyridinyl; X is O; $R^3$ is independently selected from the group consisting of alkyl and halo; m is 2; and $R^1$ and $R^2$, together with the nitrogen atom to which they are attached, form a five-membered ring containing zero additional heteroatoms wherein the remaining atoms are carbon wherein the ring is optionally substituted with one or two substituents selected from the group consisting of alkylene and alkyl.

In another embodiment the present invention provides a compound of formula (I) wherein A is pyridinyl; X is O; $R^3$ is independently selected from the group consisting of alkyl and halo; m is 2; and $R^1$ and $R^2$, together with the nitrogen atom to which they are attached, form a six-membered ring containing zero additional heteroatoms wherein the remaining atoms are carbon wherein the ring is optionally substituted with one substituent selected from the group consisting of arylalkyl and heterocyclyl.

In another embodiment the present invention provides a compound of formula (I) wherein A is pyridinyl; X is O; $R^3$ is independently selected from the group consisting of alkyl and halo; m is 2; and $R^1$ and $R^2$, together with the nitrogen atom to which they are attached, form a six-membered ring containing one additional nitrogen atom wherein the remaining atoms are carbon wherein the ring is optionally substituted with one aryl group.

In another embodiment the present invention provides a pharmaceutical composition comprising a compound of formula (I) or a therapeutically acceptable salt thereof, in combination with a therapeutically acceptable carrier.

In another embodiment the present invention provides a method for inhibiting angiogenesis in a patient in recognized need of such treatment comprising administering to the patient a therapeutically acceptable amount of a compound of formula (I), or a therapeutically acceptable salt thereof.

In another embodiment the present invention provides a method for treating cancer in a patient in recognized need of such treatment comprising administering to the patient a therapeutically acceptable amount of a compound of formula (I), or a therapeutically acceptable salt thereof.

DETAILED DESCRIPTION OF THE INVENTION

All publications, issued patents, and patent applications cited herein are hereby incorporated by reference in their entirety.

As used in the present specification the following terms have the meanings indicated:

The term "alkenyl," as used herein, refers to a straight or branched chain group of one to twelve carbon atoms derived from a straight or branched chain hydrocarbon containing at least one carbon-carbon double bond.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxycarbonyl," as used herein, refers to an alkoxy group attached to the parent molecular moiety through a carbonyl group.

The term "alkoxycarbonylalkyl," as used herein, refers to an alkoxycarbonyl group attached to the parent molecular moiety through an alkyl group.

The term "alkyl," as used herein, refers to a group of one to twelve carbon atoms derived from a straight or branched chain saturated hydrocarbon. Examples of alkyl groups include, but are not limited to, methyl, ethyl, propyl, butyl, isobutyl, 1-methylpentyl, and hexyl.

The term "alkylene," as used here, refers to a divalent group derived from a straight or branched chain hydrocarbon of from 1 to 6 carbon atoms. Representative examples of alkylene include, but are not limited to, —CH$_2$—, —CH(CH$_3$)—, —C(CH$_3$)$_2$—, —CH$_2$CH$_2$—, —CH$_2$C(CH$_3$)$_2$CH$_2$—, —CH$_2$CH$_2$CH$_2$CH$_2$—, and —CH$_2$CH(CH$_3$)CH$_2$—.

The term "alkylcarbonyl," as used herein, refers to an alkyl group attached to the parent molecular moiety through a carbonyl group.

The term "alkylsulfanyl," as used herein, refers to an alkyl group attached to the parent molecular moiety through a sulfur atom.

The term "alkylsulfanylalkyl," as used herein, refers to an alkylsulfanyl group, as defined herein, appended to the parent molecular moiety through an alkyl group, as defined herein.

The term "alkynyl," as used herein, refers to a straight or branched chain group of one to twelve carbon atoms derived from a straight or branched chain hydrocarbon containing at least one carbon-carbon triple bond.

The term "aryl," as used herein, refers to a phenyl group, or a bicyclic or tricyclic fused ring system wherein one or more of the rings is a phenyl group. Bicyclic fused ring systems consist of a phenyl group fused to a monocyclic cycloalkenyl group, a monocyclic cycloalkyl group, or another phenyl group. Tricyclic fused ring systems consist of a bicyclic fused ring system fused to a monocyclic cycloalkenyl group, a monocyclic cycloalkyl group, or another phenyl group. The aryl groups of the present invention can be attached to the parent molecular moiety through any substitutable carbon atom in the group. Representative examples of aryl groups include, but are not limited to, anthracenyl, azulenyl, fluorenyl, indanyl, indenyl, naphthyl, phenyl, and tetrahydronaphthyl. The aryl groups of the present invention can be optionally substituted with one, two, three, four, or five substituents independently selected from the group consisting of alkenyl, alkoxy, alkoxyalkyl, alkoxycarbonyl, alkyl, alkylcarbonyl, carboxy, cyano, cyanoalkyl, cycloalkyl, (cycloalkyl)alkyl, formyl, halo, haloalkoxy, haloalkyl, hydroxy, hydroxyalkyl, nitro, NR$^C$R$^D$, (NR$^C$R$^D$)alkyl, (NR$^C$R$^D$)carbonyl, and oxo.

The term "arylalkyl," as used herein, refers to an alkyl group substituted with one, two, or three aryl groups. The alkyl part of the arylalkyl can be optionally substituted with one, two, or three hydroxy groups.

The term "arylcarbonyl," as used herein, refers to an aryl group appended to the parent molecular moiety through a carbonyl group.

The term "arylcarbonylalkyl," as used herein, refers to an arylcarbonyl group appended to the parent molecular moiety through an alkyl group.

The term "aryloxy," as used herein, refers to an aryl group attached to the parent molecular moiety through an oxygen atom.

The term "carboxy," as used herein, refers to —CO$_2$H.

The term "cyano," as used herein, refers to —CN.

The term "cyanoalkyl," as used herein, refers to an alkyl group substituted with at least one cyano group.

The term "cycloalkenyl," as used herein, refers to a non-aromatic ring system having three to ten carbon atoms and one to three rings, wherein at least one ring is a five-membered ring with one double bond, a six-membered ring with one or two double bonds, a seven- or eight-membered ring with one to three double bonds, or a nine-to ten-membered ring with one to four double bonds. Examples of cycloalkenyl groups include, but are not limited to, cyclohexenyl, octahydronaphthalenyl, and norbornylenyl.

The term "cycloalkyl," as used herein, refers to a saturated ring system having three to twelve carbon atoms and one to three rings. Examples of cycloalkyl groups include, but are not limited to, cyclobutyl, cyclopropyl, cyclopentyl, cyclohexyl, cycloheptyl, bicyclo(3.1.1)heptyl, adamantyl, and bicyclo[2.2.1]heptyl. The cycloalkyl groups of this invention can be optionally substituted with one, two, three, four, or five substituents independently selected from the group consisting of alkoxy, alkoxycarbonyl, alkyl, halo, haloalkoxy, haloalkyl, hydroxy, nitro, NR$_C$R$_D$, (NR$_C$R$_D$)alkyl, (NR$_C$R$_D$)carbonyl, and oxo.

The term "(cycloalkyl)alkyl," as used herein, refers to an alkyl group substituted with one, two, or three cycloalkyl groups.

The term "(cycloalkyl)carbonyl," as used herein, refers to a cycloalkyl group appended to the parent molecular moiety through a carbonyl group.

The term "(cycloalkyl)carbonylalkyl," as used herein, refers to a (cycloalkyl)carbonyl group appended to the parent molecular moiety through an alkyl group.

The term "ethylenedioxy" as used herein, refers to a —O(CH$_2$)$_2$O— group wherein the oxygen atoms of the ethylenedioxy group are attached to the parent molecular moiety through one carbon atom to form a spirocycle.

The term "formyl," as used herein, refers to —CHO.

The terms "halo," and "halogen," as used herein, represent F, Cl, Br, and I.

The term "haloalkoxy," as used herein, refers to an alkoxy group substituted with one, two, three, or four halogen atoms.

The term "haloalkyl," as used herein, refers to an alkyl group substituted by one, two, three, or four halogen atoms.

The term "heterocyclyl," as used herein, refers to a cyclic, aromatic or non-aromatic saturated, partially unsaturated, or fully unsaturated three-, four-, five-, six-, or seven-membered ring where at least one atom is selected from the group consisting of oxygen, nitrogen, and sulfur. The term "heterocyclyl" also includes bicyclic systems where a heterocyclyl ring is fused to a phenyl group, a monocyclic cycloalkenyl group, a monocyclic cycloalkyl group, or an additional monocyclic heterocyclyl group; and tricyclic systems where a bicyclic system is fused to a phenyl group, a monocyclic cycloalkenyl group, a monocyclic cycloalkyl group, or an additional monocyclic heterocyclyl group. The heterocyclyl groups of the invention are attached to the parent molecular group through any substitutable carbon or nitrogen atom in the group. Examples of heterocyclyl groups include, but are not limited to, benzothienyl, 2,3-dihydro-1H-benzimidazolyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, tetrahydrofuranyl, thiazolyl, thienyl, and thiomorpholinyl. The heterocyclyl groups of the present invention can be optionally substituted with one, two, three, four, or five substituents independently selected from the group consisting of alkenyl, alkoxy, alkoxalkyl, alkoxycarbonyl, alkyl, alkylcarbonyl, carboxy, cyano, cyanoalkyl, cycloalkyl, (cycloalkyl)alkyl, formyl, halo, haloalkoxy, haloalkyl, hydroxy, hydroxyalkyl, nitro, NR$^C$R$^D$, (NR$^C$R$^D$)alkyl, (NR$^C$R$^D$)carbonyl, and oxo. Examples of substituted heterocycles of the present invention include, but are not limited to, 2-oxo-2,3-dihydro-1H-benzimidazolyl, The term "heterocyclylalkyl," as used herein, refers to an alkyl group substituted with one, two, or three heterocycle groups. The alkyl part of the heterocyclyl can be optionally substituted with one, two, or three hydroxy groups.

The term "heterocyclylcarbonyl," as used herein, refers to a heterocyclyl group appended to the parent molecular moiety through a carbonyl group.

The term "heterocyclylcarbonylalkyl," as used herein, refers to a heterocyclylcarbonyl group appended to the parent molecular moiety through an alkyl group.

The term "hydroxy," as used herein, refers to —OH.

The term "hydroxyalkyl," as used herein, refers to an alkyl group substituted with one, two, or three hydroxy groups.

The term "$NR^A R^B$" as used herein, means two groups, $R^A$ and $R^B$, which are appended to the parent molecular moiety through a nitrogen atom. $R^A$ and $R^B$ are independently selected from the group consisting of hydrogen, alkenyl, alkoxyalkyl, alkyl, alkynyl, alkylcarbonyl, aryl, arylalkyl, cycloalkyl, (cycloalkyl)alkyl, heterocyclyl, heterocyclylalkyl, and hydroxyalkyl.

The term "$(NR^A R^B)$alkyl" as used herein, means a $NR^A R^B$ group, as defined herein, appended to the parent molecular moiety through an alkyl group, as defined herein.

The term "$(NR^A R^B)$carbonyl" as used herein, means a $NR^A R^B$ group, as defined herein, appended to the parent molecular moiety through a carbonyl group, as defined herein.

The term "$NR^C R^D$" as used herein, means two groups, $R^C$ and $R^D$, which are appended to the parent molecular moiety through a nitrogen atom. $R^C$ and $R^D$ are independently selected from the group consisting of hydrogen, alkenyl, alkyl, and alkylcarbonyl.

The term "$(NR^C R^D)$alkyl" as used herein, means a $NR^C R^D$ group, as defined herein, appended to the parent molecular moiety through an alkyl group, as defined herein.

The term "$(NR^C R^D)$carbonyl" as used herein, means a $NR^C R^D$ group, as defined herein, appended to the parent molecular moiety through a carbonyl group, as defined herein.

The term "nitro," as used herein, refers to —$NO_2$.

The term "oxo," as used herein, refers to =O.

The term "sulfonyl," as used herein, refers to —$SO_2$—.

The compounds of the present invention can exist as therapeutically acceptable salts. The term "therapeutically acceptable salt," as used herein, refers to salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting an amino group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate, lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, amino groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric.

Asymmetric centers exist in the compounds of the present invention. These centers are designated by the symbols "R" or "S," depending on the configuration of substituents around the chiral carbon atom. It should be understood that the invention encompasses all stereochemical isomeric forms, or mixtures thereof, which possess the ability to inhibit angiogenesis and/or treat cancer. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

When it is possible that, for use in therapy, therapeutically effective amounts of a compound of formula (I), as well as therapeutically acceptable salts thereof, may be administered as the raw chemical, it is possible to present the active ingredient as a pharmaceutical composition. Accordingly, the invention further provides pharmaceutical compositions, which include therapeutically effective amounts of compounds of formula (I) or therapeutically acceptable salts thereof, and one or more pharmaceutically acceptable carriers, diluents, or excipients. The compounds of formula (I) and therapeutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of formula (I), or a therapeutically acceptable salt thereof, with one or more pharmaceutically acceptable carriers, diluents, or excipients.

Pharmaceutical formulations may be presented in unit dose forms containing a predetermined amount of active ingredient per unit dose. Such a unit may contain, for example, about 0.5 mg to about 1 gram, preferably about 1 mg to about 700 mg, more preferably about 5 mg to about 100 mg of a compound of formula (I), depending on the condition being treated, the severity of the condition, the time of administration, the route of administration, the rate of excretion of the compound employed, the duration of treatment, and the age, gender, weight, and condition of the patient, or pharmaceutical formulations may be presented in unit dose forms containing a predetermined amount of an active ingredient per dose. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intramuscular, intravenous, or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, wasces, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or an absorption agent such as betonite, kaolin, or dicalcium phosphate the powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxy ethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and therapeutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of formula (I) and therapeutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of formula (I) for the treatment of neoplastic growth, for example colon or breast carcinoma, will generally be in the range of 0.1 to 100 mg/kg body weight of recipient (mammal) per day and more usually in the range of 1 to 10 mg/kg body weight per day.

The compounds of formula (I) or therapeutically acceptable salts thereof and at least one additional cancer treatment therapy, such as an antimitotic, may be employed in combination concomitantly or sequentially in any therapeutically appropriate combination with such other anti-cancer therapies. In one embodiment, the other anti-cancer therapy is at least one additional chemotherapeutic therapy including administration of at least one anti-neoplastic agent. The administration in combination of a compound of formula (I) or therapeutically acceptable salts thereof with other anti-neoplastic agents may be in combination in accordance with the invention by administration concomitantly in (1) a unitary pharmaceutical composition including both compounds or (2) separate pharmaceutical compositions each including one of the compounds. Alternatively, the combination may be administered separately in a sequential manner wherein one anti-neoplastic agent is administered first and the other second or vice versa. Such sequential administration may be close in time or remote in time.

Determination of Biological Activity

In Vitro Assay for Angiogenic Activity

The human microvascular endothelial (HMVEC) migration assay was run according to the procedure of S. S. Tolsma, O. V. Volpert, D. J. Good, W. F. Frazier, P. J. Polverini and N. Bouck, J. Cell Biol. 122, 497-511 (1993).

The HMVEC migration assay was carried out using Human Microvascular Endothelial Cells-Dermal (single donor) and Human Microvascular Endothelial Cells, (neonatal). The BCE or HMVEC cells were starved overnight in DME containing 0.01% bovine serum albumin (BSA). Cells were then harvested with trypsin and resuspended in DME with 0.01% BSA at a concentration of $1.5 \times 10^6$ cells per mL. Cells were added to the bottom of a 48 well modified Boyden chamber (Nucleopore Corporation, Cabin John, Md.). The chamber was assembled and inverted, and cells were allowed to attach for 2 hours at 37° C. to polycarbonate chemotaxis membranes (5 μm pore size) that had been soaked in 0.01% gelatin overnight and dried. The chamber was then reinverted, and test substances (total volume of 50 μL), including activators, 15 ng/mL bFGF/VEGF, were added to the wells of the upper chamber. The apparatus was incubated for 4 hours at 37° C. Membranes were recovered, fixed and stained (Diff Quick, Fisher Scientific) and the number of cells that had migrated to the upper chamber per 3 high power fields counted. Background migration to DME+0.1 BSA was subtracted and the data reported as the number of cells migrated per 10 high power fields (400×) or, when results from multiple experiments were combined, as the percent inhibition of migration compared to a positive control.

The compounds described in Examples 1 to 97 inhibited human endothelial cell migration in the above assay at concentrations of 1 nM, 0.1 nM, or 0.01 nM as shown in Table 1.

TABLE 1

Inhibition of HMVEC migration

| % Inhibition @ 1 nM | % Inhibition @ 0.1 nM | % Inhibition @ 0.01 nM |
|---|---|---|
|  | 80 |  |
|  | 98 |  |
|  | 60 |  |
|  | 69 |  |
|  | 59 |  |
|  | 70 |  |
|  | 90 |  |
|  | 56 |  |
|  | 71 |  |
|  | 65 |  |
|  | 81 |  |
|  | 77 |  |
|  | 83 |  |
|  | 57 |  |
|  | 64 |  |
|  | 72 |  |
|  | 76 |  |
|  | 61 |  |
|  | 63 |  |
|  | 67 |  |
|  | 90 |  |
|  | 70 |  |
|  | 93 |  |
|  | 70 |  |
|  | 80 |  |
|  | 75 |  |
|  | 83 |  |
|  | 86 |  |
|  | 92 |  |
|  | 64 |  |
|  | 79 |  |
|  | 85 |  |
|  | 85 |  |
| 50 |  |  |
|  |  | 70 |
| 64 |  |  |
|  |  | 73 |
|  |  | 99 |
| 72 |  |  |
|  |  | 72 |

TABLE 1-continued

Inhibition of HMVEC migration

| % Inhibition @ 1 nM | % Inhibition @ 0.1 nM | % Inhibition @ 0.01 nM |
|---|---|---|
|  | 87 |  |
|  | 73 |  |
|  | 80 |  |
|  | 82 |  |
|  | 99 |  |
| 80 |  |  |
| 78 |  |  |
|  | 65 |  |
|  | 76 |  |
| 60 |  |  |
| 80 |  |  |
|  | 78 |  |
| 78 |  |  |
| 93 |  |  |
|  | 86 |  |
|  | 86 |  |
|  | 71 |  |
|  | 93 |  |
|  | 67 |  |
|  | 66 |  |
|  | 54 |  |
|  | 72 |  |
|  | 70 |  |
| 98 |  |  |
|  | 84 |  |
|  | 73 |  |
| 46 |  |  |
|  | 87 |  |
|  | 97 |  |
|  | 53 |  |
|  | 89 |  |
|  | 71 |  |
|  | 68 |  |
| 76 |  |  |
|  | 58 |  |
|  | 58 |  |
|  | 67 |  |
|  | 48 |  |
|  | 73 |  |
|  | 55 |  |
|  | 57 |  |
|  | 80 |  |
|  | 62 |  |
|  | 55 |  |
|  | 74 |  |
|  | 55 |  |
|  |  | 81 |
|  | 62 |  |
|  |  | 52 |
|  |  | 57 |
|  |  | 67 |
|  | 72 |  |
|  |  | 57 |
|  |  | 62 |
|  | 75 |  |
|  |  | 54 |

Many diseases (characterized as "anglogenic diseases") are driven by persistent unregulated angiogenesis. For example, ocular neovascularization has been implicated as the most common cause of blindness. In certain existing conditions such as arthritis, newly formed capillary blood vessels invade the joints and destroy cartilage. In diabetes, new capillaries formed in the retina invade the vitreous, bleed, and cause blindness. For example, ocular neovascularization has been implicated as the most common cause of blindness. In certain existing conditions such as arthritis, newly formed capillary blood vessels invade the joints and destroy cartilage. In diabetes, new capillaries formed in the retina invade the vitreous, bleed, and cause blindness. Growth and metastasis of solid tumors are also angiogenesis-dependent (Folkman, J., Cancer Res., 46: 467-473 (1986), Folkman, J., J. Natl. Cancer Inst., 82: 4-6 (1989)). It has been shown, for example, that tumors which enlarge to greater than 2 mm must obtain their own blood supply and do so by inducing the growth of new capillary blood vessels. Once these new blood vessels become embedded in the tumor, they provide a means for tumor cells to enter the circulation and metastasize to distant sites, such as the liver, the lung, and the bones (Weidner, N., et. al., N. Engl. J. Med., 324(1): 1-8 (1991)).

The compounds of the invention, including but not limited to those specified in the examples, possess antiangiogenic activity. As angiogenesis inhibitors, such compounds are useful in the treatment of both primary and metastatic solid tumors, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). Such compounds may also be useful in treating solid tumors arising from hematopoietic malignancies such as leukemias (i.e., chloromas, plasmacytomas and the plaques and tumors of mycosis fungicides and cutaneous T-cell lymphoma/leukemia) as well as in the treatment of lymphomas (both Hodgkin's and non-Hodgkin's lymphomas). In addition, these compounds may be useful in the prevention of metastases from the tumors described above either when used alone or in combination with radiotherapy and/or other chemotherapeutic agents. The compounds of the invention can also be useful in the treatment of the aforementioned conditions by mechanisms other than the inhibition of angiogenesis.

Further uses include the treatment and prophylaxis of autoimmune diseases such as rheumatoid, immune and degenerative arthritis; various ocular diseases such as diabetic retinopathy, retinopathy of prematurity, corneal graft rejection, retrolental fibroplasia, neovascular glaucoma, rubeosis, retinal neovascularization due to macular degeneration, hypoxia, angiogenesis in the eye associated with infection or surgical intervention, and other abnormal neovascularization conditions of the eye; skin diseases such as psoriasis; blood vessel diseases such as hemagiomas, and capillary proliferation within atherosclerotic plaques; Osler-Webber Syndrome; myocardial angiogenesis; plaque neovascularization; telangiectasia; hemophiliac joints; angiofibroma; and wound granulation. Other uses include the treatment of diseases characterized by excessive or abnormal stimulation of endothelial cells, including not limited to intestinal adhesions, Crohn's disease, atherosclerosis, scleroderma, and hypertrophic scars, i.e., keloids. Another use is as a birth control agent, by inhibiting ovulation and establishment of the placenta. The compounds of the invention are also useful in the treatment of diseases that have angiogenesis as a pathologic consequence such as cat scratch disease (Rochele minutesalia quintosa) and ulcers (*Helicobacter pylori*). The compounds of the invention are also useful to reduce bleeding by administration prior to surgery, especially for the treatment of resectable tumors.

Synthetic Methods

Abbreviations which have been used in the descriptions of the scheme and the examples that follow are: TFA for trifluoroacetic acid and DMSO for dimethysulfoxide.

The compounds and processes of the present invention will be better understood in connection with the following synthetic scheme which illustrates the methods by which the compounds of the invention may be prepared. Starting materials can be obtained from commercial sources or prepared by well-established literature methods known to those of ordinary skill in the art. The groups $R^1$, $R^2$, $R^3$, m, A, and X are as defined above unless otherwise noted below.

This invention is intended to encompass compounds having formula (I) when prepared by synthetic processes or by metabolic processes. Preparation of the compounds of the invention by metabolic processes include those occurring in the human or animal body (in vivo) or processes occurring in vitro.

Scheme 1

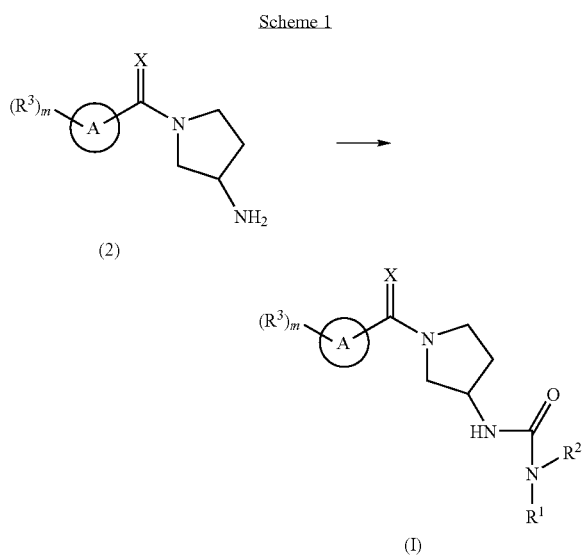

Scheme 1 shows the synthesis of compounds of formula (I). Compounds of formula (2) can be reacted with an acylating reagent such as a carbonate or 1,1'-carbonyldiimidazole then treated with an appropriately substituted amine ($HNR^1R^2$) to provide compounds of formula (I). Alternatively, compounds of formula (2) can be treated with an appropriately substituted isocyanate ($R^1NCO$) to provide compounds of formula (I) where $R^2$ is hydrogen.

The present invention will now be described in connection with certain preferred embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purposes of illustration of certain preferred embodiments and are presented to provide what is believed to be the most useful and readily understood description of its procedures and conceptual aspects.

Compounds of the invention were named by ACD/ChemSketch version 5.0 (developed by Advanced Chemistry Development, Inc., Toronto, ON, Canada) or were given names consistent with ACD nomenclature.

EXAMPLE 1

N-benzyl-N'-{(3R)-1-[(6-methylpyridin-3-yl)carbonyl]pyrrolidin-3-yl}urea

To a mixture of (3R)-1-[(6-methylpyridin-3-yl)carbonyl]pyrrolidin-3-amine bis-trifluoroacetate (0.433 g, 1.0 mmol) and triethylamine (0.418 mL, 3.0 mmol) in methylene chloride (5 ml) was added carbonyldiimidazole (0.178 g, 1.1 mmol). The reaction mixture was stirred for five hours at room temperature, at this point benzylamine (0.328 mL, 3.0 mmol) was added. The reaction mixture was stirred for additional four hours, then the solution was washed three times with water. The organic phase was dried over anhydrous sodium sulfate, filtered and the filtrate was concentrated in vacuo. The crude product was then purified by HPLC using C-18 column and a solvent mixture varying in a gradient of 10% to 90% acetonitrile/water containing 0.1% TFA. The pure fractions were lyophilized to yield 0.385 g of the title compound as the TFA salt, which subsequently was dissolved in methylene chloride (5 mL) and shaken with a MP-carbonate resin (1.0 g, substitution 2.42 mmol/g, 2.42 mmol). The resin was filtered, the filtrate was concentrated in vacuo to yield the product as the free base. The residue was dissolved in diethyl ether and to the solution was added dropwise a solution of 2M HCl in ether (2 mL, 4.0 mmol). The white precipitate was filtered and recrystallized from methanol/ethylacetate/hexane system to yield the title compound as hydrochloride salt (0.298 g), MS showed $(M+H)^+$ @ 339; NMR ($d_6$DMSO, δ): 1.71-1.90 (m, 1H), 1.98-2.19 (m, 1H), 2.69 (d, 3H), 3.17-3.37 (m, 1H), 3.43-3.74 (m, 3H), 4.04-4.27 (m, 3H), 6.18-6.73 (broad m, 2H), 7.15-7.38 (m, 5H), 7.78 (dd, 1H), 8.30-8.40 (m, 1H), 8.87 (dd, 1H).

Alternate Synthetic Procedure:

Phoxime resin (Aldrich Chemical Co.) (0.077 g, 0.14 mmol) was added to a glass reaction vessel and treated with diisopropylethylamine (0.016 g, 0.12 mmol, in 0.75 mL of methylene chloride) and (3R)-1-[(6-methylpyridin-3-yl)carbonyl]pyrrolidin-3-amine (0.013 g, 0.06 mmol, in 1.3 mL of methylene chloride). The mixture was shaken for 18 hours at room temperature to afford a resin-bound oximecarbamate intermediate that was washed with methylene chloride (3 mL). Benzylamine (0.14 mmol, in 0.6 mL of toluene) and diisopropylethylamine (0.14 mmol, in 0.75 mL of toluene) were added to the resin which was then heated to 80° C. and shaken for 18 hours. The reaction mixture was filtered and the filtrate was treated with PS-isocyanate resin (Argonaut Technologies, 0.148 g, 0.18 mmol) for 4 hours at room temperature to remove unreacted benzylamine. The product was separated from the resin by filtration and purified by HPLC as described above.

EXAMPLE 2

N-{(3R)-1-[(6-methyl-3-pyridinyl)carbonyl]-3-pyrrolidinyl}-1-pyrrolidinecarboxamide The procedure described in example 1 was used but substituting pyrrolidine instead of benzylamine. The reaction mixture was worked-up and the crude product was then purified by HPLC using C-18 column and a solvent mixture varying in a gradient of 10% to 90% acetonitrile/water containing 0.1% TFA. The pure fractions were lyophilized to yield 0.385 g of the title compound as the TFA salt. This was dissolved in methylene chloride and shaken with a MP-carbonate resin to yield the product as free base. The resin was filtered, the filtrate was concentrated in vacuo and the residue was dissolved in diethyl ether. To the solution was added drop-wise a solution of 2M HCl in ether. The white precipitate was filtered and re-crystallized from methanol/ethylacetate/hexane system to yield the title compound as hydrochloride salt; MS showed (M+H)$^+$ @ 303; NMR (d$_6$DMSO, δ): 1.73-1.83 (m, 4H), 1.84-2.13 (m, 2H), 2.71 (d, 3H), 3.12-3.30 (m, 5H), 3.32-3.43 (m, 1H), 3.60-3.75 (m, 1H), 4.12 (t, 0.5H), 4.24 (t, 0.5H), 6.16 (broad s, 1H), 7.82 (d, 1H), 8.37-8.44 (m, 1H), 8.87 (dd, 1H).

EXAMPLE 3

N-{(3R)-1-[(6-methyl-3-pyridinyl)carbonyl]-3-pyrrolidinyl}-N'-[3-(4-morpholinyl)propyl]urea The procedure described in example 1 was used but substituting 4-(3-aminopropyl)morpholine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base:

MS showed (M+H)$^+$ @ 376; NMR (d$_6$DMSO, δ): 1.45-1.63 (m, 4H), 1.70-1.85 (m, 2H), 1.97-2.15 (m, 2H), 2.15-2.44 (m, 4H), 2.50 (s, 3H), 2.94-3.2 (m, 2H), 3.45-3.69 (m, 6H), 4.02 (m, 0.5H), 4.15 (m, 0.5H), 7.33 (d, 1H), 7.79 (t, 1H), 8.57 (d, 1H).

EXAMPLE 4

N-[2-(1H-imidazol-4-yl)ethyl]-N'-{(3R)-1-[(6-methyl-3-pyridinyl)carbonyl]-3-pyrrolidinyl}urea The procedure described in example 1 was used but substituting histamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base:
MS showed (M+H)$^+$ @ 343; NMR (d$_6$DMSO, δ): 1.16-1.20 (t, 1H), 1.70-1.81 (m, 1H), 1.96-2.10 (m, 1H), 2.50 (s, 3H), 2.64-2.70 (t, 1H), 2.70-2.75 (t, 1H), 3.05-3.13 (q, 2H), 3.14-3.19 (m, 1H), 3.44-3.66 (m, 2H), 3.99-4.04 (m, 0.5H), 4.10-4.7 (m, 0.5H), 5.86-5.90 (t, 0.5H), 5.91-5.95 (t, 0.5H), 6.22-6.26 (d, 0.5H), 6.28-6.32 (d, 0.5H), 7.23-7.26 (s, 0.5H), 7.28-7.35 (m, 0.5H), 7.77-7.83 (m, 1H), 8.55-8.60 (d, 0.5H), 8.61-8.69 (d, 0.5H).

EXAMPLE 5

N-[2-(1H-indol-3-yl)ethyl]-N'-{(3R)-1-[(6-methyl-3-pyridinyl)carbonyl]-3-pyrrolidinyl}urea The procedure described in example 1 was used but substituting tryptamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 392; NMR (d$_6$DMSO, δ): 0.95-1.14 (broad m, 1H), 1.69-1.80 (m, 1H), 1.98-2.11 (m, 1H), 2.50 (s, 3H), 2.69-2.77 (t, 2H), 2.77-2.83 (t, 1H), 3.14-3.69 (m, 4H), 4.00-4.08 (m, 0.5H), 4.13-4.21 (m, 0.5H), 5.70-5.80 (m, 1H), 6.17-6.28 (dd, 1H), 6.90-7.0 (m, 1H), 7.01-7.17 (m, 1H), 7.26-7.37 (d, 2H), 7.47-7.58 (dd, 2H), 7.76-7.84 (t, 1H), 8.58-8.60 (d, 1H), 10.72-10.82 (d, 1H).

EXAMPLE 6

N-ethyl-N'-{(3R)-1-[(6-methyl-3-pyridinyl)carbonyl]-3-pyrrolidinyl}urea

The procedure described in example 1 was used but substituting ethylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 277; NMR (d$_6$DMSO, δ): 0.98 (t, 3H), 1.27-131 (m, 5H), 1.71-1.82 (m, 1H), 2.02-2.13 (m, 1H), 2.51-2.52 (d, 3H), 2.97-3.04 (q, 1H), 3.43-3.59 (m, 1H), 3.59-3.69 (m, 1H), 4.04-4.16 (m, 1H), 7.30-7.32 (d, 1H), 7.77-7.82 (dd, 1H), 8.56-8.57 (d, 1H).

EXAMPLE 7

N-isobutyl-N'-{(3R)-1-[(6-methyl-3-pyridinyl)carbonyl]-3-pyrrolidinyl}urea

The procedure described in example 1, was used but substituting isobutylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 305; NMR (d$_6$DMSO, δ): 0.81-0.83 (d, 6H), 1.54-1.69 (m, 1H), 1.69-1.83 (m, 1H), 2.00-2.15 (m, 1H), 2.51-2.52 (d, 3H), 2.79-83 (d, 2H), 3.20-3.28 (m, 1H), 3.62-3.70 (m, 1H), 4.04-4.17(broad t, 1H), 7.31-7.33 (d, 1H), 7.79-7.82 (dd, 1H), 8.57 (s, 1H).

EXAMPLE 8

N-(1-methylbutyl)-N'-{(3R)-1-[(6-methyl-3-pyridinyl)carbonyl]-3-pyrrolidinyl}urea The procedure described in example 1 was used but substituting 2-aminopentane for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 319; NMR (d$_6$DMSO, δ): 0.80-0.89 (m, 3H), 0.95-1.02 (dd, 3H), 1.17-1.37 (m, 4H), 2.47-2.52 (m, 6H), 3.40-3.69 (m, 4H), 4.04-4.16 (m, 1H), 7.30-7.32 (d, 1H), 7.77-7.81 (dd, 1H), 8.56 (d, 1H).

EXAMPLE 9

N-{(3R)-1-[(6-methyl-3-pyridinyl)carbonyl]-3-pyrrolidinyl}-N'-neopentylurea

The procedure described in example 1 was used but substituting neopentylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 319; NMR (d$_6$DMSO, δ): 0.78-0.85 (broad s, 10H), 1.70-1.83 (m, 1H), 2.01-2.15 (m, 1H), 2.50-2.52 (d, 5H), 2.78-2.83 (broad s, 2H), 3.44-3.58 (m, 0.5H), 3.60-3.70 (m, 0.5H), 4.05-4.17 (m, 1H), 7.29-7.33 (d, 1H), 7.78-7.81 (dd, 1H), 8.57 (d, 1H).

EXAMPLE 10

N-(3,3-dimethylbutyl)-N'-{(3R)-1-[(6-methyl-3-pyridinyl)carbonyl]-3-pyrrolidinyl}urea The procedure described in example 1 was used but substituting 3,3-dimethylbutylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 333; NMR (d$_6$DMSO, δ): 0.84-0.89 (broad s, 10H), 1.25-1.34 (m, 1H), 2.45-2.49 (m, 9H), 2.97-3.03 (m, 2H), 3.60-3.68 (m, 1H), 7.30-7.33 (d, 1H), 7.78-7.81 (dd, 1H), 8.56-8.57 (d, 1H).

EXAMPLE 11

N-{(3R)-1-[(6-methyl-3-pyridinyl)carbonyl]-3-pyrrolidinyl}-N'-(2,2,2-trifluoroethyl)urea The procedure described in example 1 was used but substituting 2,2,2-trifluoroethylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 331; NMR (d$_6$DMSO, δ): 1.72-1.86 (m, 1H), 2.03-2.17 (m, 1H), 2.51 (d, 3H), 3.42-3.60 (m, 3H), 3.62-3.72 (m, 1H), 3.72-3.85 (m, 2H), 4.08-4.20 (broad m, 1H), 6.19-6.28 (m, 1H), 6.28-6.38 (m, 1H), 7.30-7.33 (d, 1H), 7.78-7.82 (dd, 1H), 8.57-8.58 (d, 1H).

EXAMPLE 12

N-(2-methoxy-1-methylethyl)-N'-{(3R)-1-[(6-methyl-3-pyridinyl)carbonyl]-3-pyrrolidinyl}urea The procedure described in example 1 was used but substituting 2-amino-1-methoxypropane for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 321; NMR (d$_6$DMSO, δ): 0.96-1.04 (dd, 3H), 1.68-1.82 (m, 1H), 1.99-2.14 (m, 1H), 2.47-2.52 (m, 9H), 3.44-3.59 (m, 2H), 3.59-3.77 (m, 2H), 4.03-4.16 (m, 1H), 7.29-7.35 (d, 1H), 7.78-7.82 (dd, 1H), 8.55-8.60 (d, 1H).

EXAMPLE 13

N-(2-ethoxyethyl)-N'-{(3R)-1-[(6-methyl-3-pyridinyl)carbonyl]-3-pyrrolidinyl}urea The procedure described in example 1 was used but substituting 2-ethoxyethylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 321; NMR (d$_6$DMSO, δ): 1.06-1.14 (t, 3H), 1.71-1.81 (m, 1H), 2.01-2.14 (m, 1H), 2.43-2.44 (m, 4H), 2.49-2.53 (d, 3H), 3.10-3.17 (t, 2H), 3.31-3.37 (m, 2H), 3.39-3.47 (m, 2H), 3.60-3.69 (m, 0.5H), 4.05-4.17 (m, 0.5H), 7.30-7.32 (d, 1H), 7.77-7.81 (dd, 1H), 8.56-8.57 (d, 1H).

EXAMPLE 14

N-{(3R)-1-[(6-methyl-3-pyridinyl)carbonyl]-3-pyrrolidinyl}-N'-(tetrahydro-3-furanylmethyl)urea The procedure described in example 1 was used but substituting 3-aminomethyltetrahydrofuran for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 333; NMR (d$_6$DMSO, δ): 1.41-1.57 (m, 1H), 1.69-1.94 (m, 2H), 2.00-2.14 (m, 1H), 2.19-2.35 (m, 1H), 2.49-2.53 (d, 3H), 2.95-3.02 (d, 2H), 3.44-3.72 (m, 7H), 4.04-4.15 (m, 1H), 5.59-6.04 (broad m, 1H), 7.28-7.32 (d, 1H), 7.77-7.80 (dd, 1H), 8.56 (d, 1H).

EXAMPLE 15

N-(cyanomethyl)-N'-{(3R)-1-[(6-methyl-3-pyridinyl)carbonyl]-3-pyrrolidinyl}urea

The procedure described in example 1 was used but substituting aminoacetonitrile for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 288; NMR (d$_6$DMSO, δ): 1.72-1.87 (m, 1H), 2.03-2.17 (m, 1H), 2.52 (d, 3H), 3.22-3.32 (m, 1H), 3.63-3.75 (m, 1H), 4.00 (broad s, 2H), 4.08-4.19 (board m, 1H), 6.22-6.33 (broad m, 1H), 6.40-6.52 (broad m, 1H), 7.30-7.33 (d, 1H), 7.78-7.82 (dd, 1H), 8.57-8.58 (d, 1H).

EXAMPLE 16

N-{(3R)-1-[(6-methyl-3-pyridinyl)carbonyl]-3-pyrrolidinyl}-N'-2-propynylurea

The procedure described in example 1 was used but substituting propargylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed $(M+H)^+$ @ 287; MS showed $(M+H)^+$ @ 288; NMR ($d_6$DMSO, δ): 2.47-2.48 (m, 5H), 2.52 (s, 1H), 2.51 (broad s, 3H), 2.82-2.83 (t, 1H), 3.76-3.79 (broad m, 2H), 7.28-7.31 (d, 1H), 7.76-7.80 (dd, 1H), 8.56-8.57 (d, 1H)

EXAMPLE 17

N-(cyclopropylmethyl)-N'-{(3R)-1-[(6-methyl-3-pyridinyl)carbonyl]-3-pyrrolidinyl}urea The procedure described in example 1 was used but substituting cyclopropylmethylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed $(M+H)^+$ @ 303; This was dissolved in methylene chloride and shaken with a MP-carbonate resin to yield the desired product as the free base: MS showed $(M+H)^+$ @ 288; NMR ($d_6$DMSO, δ): 0.08-0.14 (m, 2H), 0.33-0.41 (m, 2H), 0.81-0.89 (broad m, 1H), 1.72-1.82 (broad m, 1H), 2.01-2.14 ((broad m, 1H), 2.47-2.49 (m, 4H), 2.51 (broad s, 3H), 2.87-2.89 (broad d, 1H), 3.47-3.52 (broad m, 1H), 3.62-3.69 (broad m, 1H), 7.30-7.33 (d, 1H), 7.78-7.81 (dd, 1H), 8.57-8.58 (d, 1H).

EXAMPLE 18

N-cyclobutyl-N'-{(3R)-1-[(6-methyl-3-pyridinyl)carbonyl]-3-pyrrolidinyl}urea

The procedure described in example 1 was used but substituting cyclobutylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed $(M+H)^+$ @ 303; NMR ($d_6$DMSO, δ): 1.48-1.65 (m, 2H), 1.70-1.83 (m, 2H), 1.99-2.21 (m, 2H), 2.51 (broad s, 3H), 3.17-3.27 (m, 1H), 3.60-3.67 (m, 4H), 3.59-4.15 (m, 2H), 5.73-6.01 (broad m, 1H), 7.30-7.33 (d, 1H), 7.78-7.82 (dd, 1H), 8.57-8.58 (d, 1H).

EXAMPLE 19

N-cyclohexyl-N'-{(3R)-1-[(6-methyl-3-pyridinyl)carbonyl]-3-pyrrolidinyl}urea

The procedure described in example 1 was used but substituting cyclohexylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed $(M+H)^+$ @ 331; NMR ($d_6$DMSO, δ): 1.01-1.33 (m, 4H), 1.45-1.56 (m, 1H), 1.56-1.68 (m, 2H), 1.68-1.82 (m, 3H), 2.00-2.15 (broad m, 1H), 2.48 (m, 4H), 3.17-3.27 (m, 1H), 3.31-3.43 (m, 1H), 3.43-3.59 (m, 2H), 4.04-4.17 (m, 2H), 7.32-7.35 (d, 1H), 7.80-7.83 (dd, 1H), 8.57-8.58 (d, 1H).

EXAMPLE 20

N-(4-methylcyclohexyl)-N'-{(3R)-1-[(6-methyl-3-pyridinyl)carbonyl]-3-pyrrolidinyl}urea The procedure described in example 1 was used but substituting 4-methylcyclohexylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed $(M+H)^+$ @ 345; NMR ($d_6$DMSO, δ): 0.84-0.89 (q, 3H), 0.91-1.16 (m, 3H), 1.22-1.34 (broad m, 1H), 1.40-1.52 (broad m, 4H), 1.57-1.84 (m, 4H), 1.99-2.15 (m, 1H), 2.51 (d, 3H), 3.18-3.28 (m, 2H), 4.04-4.16 (broad m, 1H), 7.30-7.33 (d, 1H), 7.79-7.82 (dd, 1H), 8.57-8.58 (d, 1H).

EXAMPLE 21

N-(cyclohexylmethyl)-N'-{(3R)-1-[(6-methyl-3-pyridinyl)carbonyl]-3-pyrrolidinyl}urea The procedure described in example 1 was used but substituting cyclohexylmethylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed $(M+H)^+$ @ 345; NMR ($d_6$DMSO, δ): 0.79-0.94 (m, 2H), 1.07-1.23 (m, 3H), 1.23-1.40 (m, 1H), 1.52-1.70 (m, 5H), 1.70-1.81 (m, 1H), 2.01-2.13 (m, 1H), 2.51 (d, 3H), 2.83-2.85 (d, 2H), 3.17-3.27 (m, 1H), 3.43-3.72 (m, 3H), 4.05-4.15 (broad m, 1H), 7.31-7.34 (d, 1H), 7.79-7.83 (dd, 1H), 8.56-8.57 (d, 1H).

EXAMPLE 22

N-cycloheptyl-N'-{(3R)-1-[(6-methyl-3-pyridinyl)carbonyl]-3-pyrrolidinyl}urea

The procedure described in example 1 was used but substituting cycloheptylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)+ @ 345; NMR (d$_6$DMSO, δ): 0.98-1.14 (broad s, 1H), 1.69-1.803 (m, 1H), 1.96-2.11 (m, 1H), 2.50 (s, 3H), 2.70-2.82 (m, 6H), 3.16-3.17 (m, 1H), 3.45-3.51 (m, 2H), 3.51-3.64 (m, 1H), 3.64-3.74 (m, 2H), 4.05 (m, 0.5H), 4.17 (m, 0.5H), 5.72-5.78 (m, 1H), 6.19-6.25 (m, 1H), 6.92-7.13 (m, 3H), 7.33 (m, 2H), 7.49-7.55 (m, 1H), 7.79-7.82 (m, 1H).

EXAMPLE 23

N-[(1S)-1-(hydroxymethyl)-3-methylbutyl]-N'-{(3R)-1-[(6-methyl-3-pyridinyl)carbonyl]-3-pyrrolidinyl}urea The procedure described in example 1 was used but substituting (2S)-2-amino-4-methylpentan-1-ol for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)+ @ 349; NMR (d$_6$DMSO, δ): 0.83-0.90 (t, 6H), 1.15-1.37 (m, 2H), 1.54-1.67 (m, 1H), 1.68-1.83 (m, 1H), 2.04-2.19 (m, 1H), 2.51-2.52 (d, 3H), 2.69 (s, 1H), 3.25-3.35 (m, 2H), 3.46-3.67 (broad m, 5H), 4.06-4.16 (broad m, 1H), 7.28-7.31 (d, 1H), 7.76-7.79 (dd, 1H), 8.56 (d, 1H).

EXAMPLE 24

N-[(1R)-1-(hydroxymethyl)-3-methylbutyl]-N'-{(3R)-1-[(6-methyl-3-pyridinyl)carbonyl]-3-pyrrolidinyl}urea The procedure described in example 1 was used but substituting (2R)-2-amino-4-methylpentan-1-ol for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)+ @ 349; NMR (d$_6$DMSO, δ): 0.80-0.87 (t, 6H), 1.12-1.37 (m, 2H), 1.49-1.65 (m, 1H), 1.67-1.81 (m, 1H), 2.02-2.19 (m, 1H), 2.51-2.52 (d, 3H), 2.69 (s, 1H), 3.18-3.29 (m, 2H), 3.43-3.67 (broad m, 5H), 4.04-4.14 (broad m, 1H), 7.29-7.32 (d, 1H), 7.76-7.80 (dd, 1H), 8.56 (d, 1H).

EXAMPLE 25

N-[(1S)-2-hydroxy-1-phenylethyl]-N'-{(3R)-1-[(6-methyl-3-pyridinyl)carbonyl]-3-pyrrolidinyl}urea The procedure described in example 1 was used but substituting (2S)-2-amino-2-phenylethanol for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)+ @ 369; NMR (d$_6$DMSO, δ): 1.70-1.80 (m, 1H), 1.82-1.96 (m, 1H), 2.00-2.19 (m, 2H), 2.51-2.52 (d, 3H), 2.69 (s, 1H), 2.67-2.97 (broad m, 1H), 3.17-3.34 (m, 2H), 3.59-3.68 (broad m, 2H), 4.03-4.14 (broad s, 1H), 4.61-4.68 (broad t, 1H), 5.97-6.26 (broad m, 1H), 7.14-7.33 (m, 6H), 7.78-7.82 (dd, 1H), 8.57 (d, 1H).

EXAMPLE 26

N-(3-isopropoxypropyl)-N'-{(3R)-1-[(6-methyl-3-pyridinyl)carbonyl]-3-pyrrolidinyl}urea The procedure described in example 1 was used but substituting 3-isopropoxypropylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)+ @ 349; NMR (d$_6$DMSO, δ): 1.05-1.07 (d, 6H), 1.50-1.61 (m, 2H), 1.71-1.81 (m, 1H) 1.86-1.94 (m, 1H), 2.02-2.19 (m, 2H), 2.51-2.52 (d, 3H), 2.69 (s, 1H), 3.00-3.05 (m, 2H), 3.30-3.36 (m, 2H), 3.45-3.54 (m, 2H), 3.61-3.68 (m, 2H), 4.07-4.15 (broad t, 1H), 5.83-6.05 (broad m, 1H), 7.29-7.31 (d, 1H), 7.76-7.80 (dd, 1H), 8.56-8.58 (d, 1H).

EXAMPLE 27

N-(2,3-dihydroxypropyl)-N'-{(3R)-1-[(6-methyl-3-pyridinyl)carbonyl]-3-pyrrolidinyl}urea The procedure described in example 1 was used but substituting 3-amino-1,2-propanediol for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)+ @ 323; NMR (d$_6$DMSO, δ): 1.73-1.82 (m, 1H), 2.02-2.12 (m, 1H), 2.51(d, 3H), 2.92-2.98 (m, 1H), 3.12-3.18 (dd, 1H), 3.26-3.32 (m, 5H), 3.62-3.68 (m, 2H), 4.06-4.16 (broad m, 1H), 7.29-7.33 (d, 1H), 7.78-7.82 (dd, 1H), 8.57 (d, 1H).

EXAMPLE 28

N-{(3R)-1-[(6-methyl-3-pyridinyl)carbonyl]-3-pyrrolidinyl}-N'-[2-(2-thienyl)ethyl]urea The procedure described in example 1 was used but substituting 2-thien-2-ylethylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)+ @ 356.

EXAMPLE 29

N-[2-(5-methoxy-1H-indol-3-yl)ethyl]-N'-{(3R)-1-[(6-methyl-3-pyridinyl)carbonyl]-3-pyrrolidinyl}urea The procedure described in example 1 was used but substituting 2-(5-methoxy-1H-indol-3-yl)ethylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 422; NMR (d$_6$DMSO, δ): 1.79-1.82 (m, 1H), 1.86-1.95 (m, 1H), 2.00-2.15(m, 2H), 2.51-2.52 (d, 3H), 2.69 (s, 1H), 2.73-2.78 (t, 2H), 3.43-3.56 (m, 2H), 3.63-3.70 (m, 2H), 3.75 (s, 3H), 4.07-4.18 (broad m, 1H), 6.69-6.73 (dd, 1H), 7.00-7.01 (d, 1H), 7.04 (s, 1H), 7.19-7.22 (d, 1H), 7.29-7.32 (d, 1H), 7.77-7.80 (dd, 1H), 8.56-8.57 (d, 1H).

EXAMPLE 30

N-(2,4-difluorobenzyl)-N'-{(3R)-1-[(6-methyl-3-pyridinyl)carbonyl]-3-pyrrolidinyl}urea The procedure described in example 1 was used but substituting 2,3-difluorobenzylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 375; NMR (d$_6$DMSO, δ): 1.69-1.96 (m, 2H), 2.03-2.19 (m, 1H), 2.51-2.52 (d, 3H), 3.21-3.32 (m, 1H), 3.43-3.60 (m, 2H), 3.60-3.71 (m, 1H), 4.07-4.16 (broad m, 1H), 4.20 (broad s, 1H), 6.04-6.18 (broad m, 1H), 6.92-7.09 (m, 2H), 7.28-7.38 (m, 2H), 7.74-7.79 (dd, 1H), 8.55 (d, 1H).

EXAMPLE 31

N-(3,3-diphenylpropyl)-N'-{(3R)-1-[(6-methyl-3-pyridinyl)carbonyl]-3-pyrrolidinyl}urea The procedure described in example 1 was used but substituting 3,3-diphenylpropylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 443; NMR (d$_6$DMSO, δ): 1.71-1.81 (m, 1H), 1.86-1.97 (m, 1H), 2.00-2.19 (m, 3H), 2.51-2.52 (d, 3H), 2.88-2.93 (t, 2H), 3.20-3.32 (m, 2H), 3.57-3.67 (m, 1H), 3.92-3.97 (t, 1H), 4.04-4.13 (broad m, 1H), 7.10-7.19 (m, 1H), 7.23-7.31 (m, 10H), 7.77-7.81 (dd, 1H), 8.56 (d, 1H).

EXAMPLE 32

N-[(1R)-2-hydroxy-1-phenylethyl]-N'-{(3R)-1-[(6-methyl-3-pyridinyl)carbonyl]-3-pyrrolidinyl}urea The procedure described in example 1 was used but substituting (2R)-2-amino-2-phenylethanol for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 369; NMR (d$_6$DMSO, δ): 1.72-1.82 (m, 2H), 1.86-1.96 (m, 2H), 2.03-2.19 (m, 2H), 2.47-2.49 (m, 2H), 2.50-2.52 (d, 3H), 2.69 (m, 1H), 3.15-3.33 (m, 1H), 3.52-3.66 (m, 1H), 4.06-4.14 (broad m, 1H), 4.63-4.67 (m, 1H), 7.16-7.31 (m, 8H), 7.76-7.79 (dd, 1H), 8.56 (d, 1H).

EXAMPLE 33

N-{(3R)-1-[(6-methylpyridin-3-yl)carbonyl]pyrrolidin-3-yl}-N'-[(1S)-1-phenylethyl]urea The procedure described in example 1 was used but substituting (1S)-1-phenylethylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 353; NMR (d$_6$DMSO, δ): 1.72-1.82 (m, 2H), 1.86-1.96 (m, 2H), 2.03-2.19 (m, 2H), 2.47-2.49 (m, 2H), 2.50-2.52 (d, 3H), 2.69 (m, 1H), 3.15-3.33 (m, 1H), 3.52-3.66 (m, 1H), 4.06-4.14 (broad m, 1H), 4.63-4.67 (m, 1H), 7.16-7.31 (m, 8H), 7.76-7.79 (dd, 1H), 8.56 (d, 1H).

EXAMPLE 34

N,N-dibutyl-N'-{(3R)-1-[(2-chloro-6-methylpyridin-3-yl)carbonyl]pyrrolidin-3-yl}urea The procedure described in example 1 was used but substituting 2-chloro-6-methylnicotinic acid for 6-methylnicotinic acid and dibutylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt: MS showed (M+H)$^+$ @ 395; NMR (d$_6$DMSO, δ): 0.84-0.90 (m, 6H), 1.15-1.26 (m, 6H), 1.33-1.44 (m, 6H), 1.85-2.11 (m, 2H), 2.48-2.49 (m, 3H), 2.96-3.00 (m, 0.5H), 3.03-3.19 (m, 1.5H), 3.22-3.28 (m, 1H), 3.35-3.38 (m, 0.5H), 3.43-3.49 (m, 0.5H), 3.62-3.67 (m, 1H), 4.07-4.11 (m, 0.5H), 4.18-4.22 (m, 0.5H), 6.05-6.11 (dd, 1H), 7.35-7.38 (m, 1H), 7.73-7.76 (m, 1H).

EXAMPLE 35

N'-{(3R)-1-[(2-chloro-6-methylpyridin-3-yl)carbonyl]pyrrolidin-3-yl}-N-isopropyl-N-(2-methoxyethyl)urea The procedure described in example 1 was used but substituting 2-chloro-6-methylnicotinic acid for 6-methylnicotinic acid and N-(2-methoxyethyl)isopropylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt: MS showed (M+H)$^+$ @ 383; NMR (d$_6$DMSO, δ): 0.99-1.00 (d, 4H), 1.03-1.04 (d, 2.5H), 1.15 (s, 0.5H), 1.08-1.88 (m, 1H), 2.01-2.12 (m, 1H), 2.48 (s, 3H), 3.17-3.24 (m, 2H), 3.26-3.27 (d, 3H), 3.35-3.40 (m, 3H), 3.46-3.51 (m, 1H), 3.58-3.68 (m, 1H), 4.04-4.08 (m, 0.5H), 4.15-4.23 (m, 1.5H), 6.28-6.33 (dd, 1H), 7.35-7.38 (m, 1H), 7.73-7.78 (dd, 1H).

EXAMPLE 36

N-{(3R)-1-[(2-chloro-6-methylpyridin-3-yl)carbonyl]pyrrolidin-3-yl}-1,3,3-trimethyl-6-azabicyclo [3.2.1]octane-6-carboxamide The procedure described in example 1 was used but substituting 2-chloro-6-methylnicotinic acid for 6-methylnicotinic acid and 1,3,3-trimethyl-6-azabicyclo[3.2.1]octane for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt: MS showed (M+H)$^+$ @ 383; NMR (d$_6$DMSO, δ): 0.83 (broad m, 1H), 0.87-0.89 (broad d, 4H), 1.00-1.02 (dd, 3H), 1.13-1.19 (m, 1H), 1.20-1.28 (m, 1H), 1.33-1.45 (m, 2H), 1.53-1.63 (m, 1H), 1.68-1.72 (d, 0.5H), 1.77-1.80 (d, 0.5H), 1.84-1.91 (m, 1H), 1.96-2.00 (m, 0.5H), 2.05-2.09 (m, 0.5H), 2.48 (s, 3H), 2.52-2.54 (d, 1H), 2.82-2.97 (m, 1H), 3.12-3.18 (m, 1H), 3.29 (m, 2H), 3.61-3.67 (m, 1H), 4.01-4.13 (m, 1.5H), 4.17-4.20 (m, 0.5H), 5.96-6.04 (m, 1H), 7.35-7.38 (t, 1H), 7.72-7.77 (m, 1H).

EXAMPLE 37

N-{(3R)-1-[(2-chloro-6-methylpyridin-3-yl)carbonyl]pyrrolidin-3-yl}-N'-[(1R)-2-hydroxy-1-phenylethyl]urea The procedure described in example 1 was used but substituting 2-chloro-6-methylnicotinic acid for 6-methylnicotinic acid and (2R)-2-amino-2-phenylethanol for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 383; NMR (d$_6$DMSO, δ): 1.70-1.80 (m, 1H), 2.02-2.15 (m, 1H), 2.46 (s, 3H), 3.09 (s, 1H), 3.18-3.37 (m, 1H), 3.48-3.63 (m, 4H), 6.06-6.21 (m, 2H), 7.16-7.33 (m, 6H), 7.60-7.69 (m, 1H).

EXAMPLE 38

N-{(3R)-1-[(2-chloro-6-methylpyridin-3-yl)carbonyl]pyrrolidin-3-yl}-N'-(3-ethoxypropyl)urea The procedure described in example 1 was used but substituting 2-chloro-6-methylnicotinic acid for 6-methylnicotinic acid and 3-ethoxypropylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 369; NMR (d$_6$DMSO, δ): 1.06-1.14 (m, 4H), 1.54-1.64 (m, 2H), 1.70-1.81 (m, 0.5H), 2.02-2.15 (m, 0.5H), 2.49 (s, 3H), 2.88-2.96 (m, 2H), 3.03-3.09 (m, 2H), 3.15-3.25 (m, 1H), 3.31-3.42 (m, 4H), 5.52-5.65 (m, 1H), 5.89-5.94 (m, 1H), 7.30-7.33 (d, 1H), 7.66-7.71 (m, 1H).

EXAMPLE 39

N-{(3R)-1-[(2-chloro-6-methylpyridin-3-yl)carbonyl]pyrrolidin-3-yl}-N'-(3-isopropoxypropyl)urea The procedure described in example 1 was used but substituting 2-chloro-6-methylnicotinic acid for 6-methylnicotinic acid and 3-isopropoxypropylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 383; NMR (d$_6$DMSO, δ): 1.03-1.10 (m, 6H), 1.50-1.53 (m, 1H), 2.47-2.49 (m, 7H), 3.01 (m, 4H), 3.31-3.37 (m, 2H), 3.47-3.52 (m, 1H), 7.29-7.32 (d, 1H), 7.66-7.69 (m, 1H).

EXAMPLE 40

N-{(3R)-1-[(2-chloro-6-methylpyridin-3-yl)carbonyl]pyrrolidin-3-yl}-N'-(3-isobutoxypropyl)urea The procedure described in example 1 was used but substituting 2-chloro-6-methylnicotinic acid for 6-methylnicotinic acid and 3-isobutoxypropylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M–H)$^+$ @ 395; NMR (d$_6$DMSO, δ): 0.83-0.87 (m, 6H), 1.56-1.62 (m, 1H), 1.72-1.80 (m, 1H), 2.49 (m, 5H), 3.01 (m, 6H), 3.08-3.14 (m, 2H), 3.32-3.39 (m, 2H), 5.56-5.64 (m, 1H), 5.88-5.93 (m, 1H), 7.30-7.32 (d, 1H), 7.66-7.69 (m, 1H).

EXAMPLE 41

N-{(3R)-1-[(2-chloro-6-methylpyridin-3-yl)carbonyl]pyrrolidin-3-yl}-N'-[3-(methylthio)propyl]urea The procedure described in example 1 was used but substituting 2-chloro-6-methylnicotinic acid for 6-methylnicotinic acid and 3-methylthiopropylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 371; NMR (d$_6$DMSO, δ): 1.57-1.67 (m, 1H), 2.02-2.05 (m, 3H), 2.49 (s, 6H), 2.97 (s, 1H), 3.01 (s, 7H), 3.08 (s, 1H), 7.30-7.32 (d, 1H), 7.68-7.71 (m, 1H).

EXAMPLE 42

N-benzyl-N'-{(3R)-1-[(2-chloro-6-methylpyridin-3-yl)carbonyl]pyrrolidin-3-yl}-N-ethylurea The procedure described in example 1 was used but substituting 2-chloro-6-methylnicotinic acid for 6-methylnicotinic acid and N-ethylbenzylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 401; NMR (d$_6$DMSO, δ): 0.93-0.99 (t, 3H), 2.49 (d, 3H), 3.01 (broad m, 4H), 3.16-3.21 (m, 2H), 4.39-4.44 (d, 2H), 7.16-7.31 (m, 5H), 7.30-7.32 (d, 1H), 7.65-7.68 (d, 1H).

EXAMPLE 43

N,N-dibenzyl-N'-{(3R)-1-[(2-chloro-6-methylpyridin-3-yl)carbonyl]pyrrolidin-3-yl}urea The procedure described in example 1 was used but substituting 2-chloro-6-methylnicotinic acid for 6-methylnicotinic acid and N,N-dibenzylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 463; NMR (d$_6$DMSO, δ): 1.82-1.89 (m, 1H), 2.02-2.10 (m, 1H), 2.47-2.48 (m, 4H), 2.49 (d, 3H), 3.12-3.19 (m, 0.5H), 3.35-3.41 (m, 0.5H), 4.37 (s, 2H), 4.42 (s, 2H), 7.13-7.32 (m, 11H), 7.61-7.85 (m, 1H).

EXAMPLE 44

N'-{(3R)-1-[(2-chloro-6-methylpyridin-3-yl)carbonyl]pyrrolidin-3-yl}-N-methyl-N-(2-phenylethyl)urea The procedure described in example 1 was used but substituting 2-chloro-6-methylnicotinic acid for 6-methylnicotinic acid and N-methyl-N-(2-phenylethyl)amine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 401; NMR (d$_6$DMSO, δ): 1.81-1.91 (m, 1H), 1.98-2.13 (m, 1H), 2.47 (s, 3H), 2.73 (s, 3H), 2.76 (s, 2H), 2.91-2.99 (m, 1H), 3.13-3.18 (m, 1H), 3.25-3.48 (m, 2H), 3.60-3.75 (m, 1H), 4.05-4.21 (m, 1H), 5.82-5.96 (m, 1H), 7.13-7.27 (m, 5H), 7.30-7.33 (d, 1H), 7.67-7.71 (m, 1H).

EXAMPLE 45

N'-{(3R)-1-[(2-chloro-6-methylpyridin-3-yl)carbonyl]pyrrolidin-3-yl}-N-[2-(3,4-dimethoxyphenyl)ethyl]-N-methylurea The procedure described in example 1 was used but substituting 2-chloro-6-methylnicotinic acid for 6-methylnicotinic acid and N-[2-(3,4-dimethoxyphenyl)ethyl]-N-methylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 461; NMR (d$_6$DMSO, δ): 1.80-2.07 (broad m, 2H), 2.47-2.48 (d, 3H), 2.49 (d, 3H), 2.49 (d, 3H), 2.61-2.69 (m, 2H), 2.72-2.76 (d, 4H), 3.28-3.42 (m, 2H), 3.71-3.75 (m, 6H), 6.69-6.83 (m, 3H), 7.30-7.32 (d, 1H), 7.67-7.71 (m, 1H).

EXAMPLE 46

4-benzyl-N-{(3R)-1-[(2-chloro-6-methylpyridin-3-yl)carbonyl]pyrrolidin-3-yl}piperidine-1-carboxamide The procedure described in example 1 was used but substituting 2-chloro-6-methylnicotinic acid for 6-methylnicotinic acid and 4-benzylpiperidine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 441; NMR (d$_6$DMSO, δ): 0.93-1.08 (m, 2H), 1.48-1.57 (m, 2H), 1.61-1.72 (m, 1H), 1.81-1.91 (m, 1H), 1.99-2.12 (m, 1H), 2.49 (d, 3H), 2.47-2.48 (d, 4H), 2.50-2.53 (m, 2H), 2.59-2.64 (d, 1H), 3.30-3.37 (m, 0.5H), 3.62-3.71 (m, 0.5H), 3.83-3.93 (m, 1H), 4.07-4.13 (m, 1H), 6.11-6.18 (m, 1H), 7.13-7.32 (m, 6H), 7.66-7.71 (m, 1H).

EXAMPLE 47

N-{(3R)-1-[(2-chloro-6-methylpyridin-3-yl)carbonyl]pyrrolidin-3-yl}-4-(2-oxo-2,3-dihydro-1H-benzimidazol-1-yl)piperidine-1-carboxamide The procedure described in example 1 was used but substituting 2-chloro-6-methylnicotinic acid for 6-methylnicotinic acid and 1-piperidin-4-yl-1,3-dihydro-2H-benzimidazol-2-one for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 483.

EXAMPLE 48

N-{(3R)-1-[(2-chloro-6-methylpyridin-3-yl)carbonyl]pyrrolidin-3-yl}-4-phenylpiperazine-1-carboxamide The procedure described in example 1 was used but substituting 2-chloro-6-methylnicotinic acid for 6-methylnicotinic acid and 1-phenylpiperazine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 426; NMR (d$_6$DMSO, δ): 1.23-1.33 (m, 1H), 1.86-1.95 (m, 1H), 2.00-2.15 (m, 1H), 2.47 (d, 3H), 2.94 (m, 3H), 3.08-3.13 (m, 4H), 3.35-3.52 (m, 3H), 3.59-3.76 (m, 1H), 4.06-4.26 (m, 1H), 6.27-6.40 (m, 1H), 6.73-6.83 (m, 1H), 6.88-6.97 (m, 2H), 7.15-7.34 (m, 3H).

EXAMPLE 49

N-[2-(diethylamino)ethyl]-N-methyl-N'-{(3R)-1-[(6-methylpyridin-3-yl)carbonyl]pyrrolidin-3-yl}urea The procedure described in example 1 was used but substituting N-[2-(diethylamino)ethyl]-N-methylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the bis-TFA salt: MS showed (M+H)$^+$ @ 362; NMR (d$_6$DMSO, δ): 1.25-1.26 (m, 6H), 2.11-2.20 (m, 1H), 2.50-2.52 (m, 3H), 2.96-3.02 (m, 4H), 3.10-3.30 (m, 4H), 3.42-3.47 (m, 0.5H), 3.55-3.60 (m, 3H), 3.67-3.70 (m, 1H), 3.76-3.99 (m, 3H), 4.20-4.24 (m, 0.5H), 4.53-4.69 (d, 1H), 7.05-7.14 (m, 2H), 7.84-7.85 (d, 1H).

EXAMPLE 50

N-benzyl-N-ethyl-N'-{(3R)-1-[(6-methylpyridin-3-yl)carbonyl]pyrrolidin-3-yl}urea The procedure described in example 1 was used but substituting N-benzyl-N-ethylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt: MS showed (M+H)$^+$ @ 367; NMR (d$_6$DMSO, δ): 1.02-1.06 (m, 3H), 1.96-2.03 (m, 1H), 2.09-2.17 (m, 1H), 2.52 (s, 3H), 3.35-3.49 (m, 3H), 3.60-3.63 (m, 0.5H), 3.69-3.74 (m, 0.5H), 3.83-3.88 (m, 1H), 3.96-3.99 (m, 0.5H), 4.18-4.22 (m, 0.5H), 4.65-4.70 (m, 2.5H), 4.80-4.83 (m, 0.5H), 6.63-6.64 (d, 1H), 7.05-7.13 (dd, 1H), 7.27-7.40 (m, 5H), 7.76-7.78 (dd, 1H), 8.86-8.90 (m, 1H).

EXAMPLE 51

N-benzyl-N-isopropyl-N'-{(3R)-1-[(6-methylpyridin-3-yl)carbonyl]pyrrolidin-3-yl}urea The procedure described in example 1 was used but substituting N-benzyl-N-isopropylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt: MS showed (M+H)$^+$ @ 381; NMR (d$_6$DMSO, δ): 1.03-1.09 (m, 6H), 1.86-1.91 (m, 1H), 2.02-2.11 (m, 1H), 2.52 (broad s, 3H), 3.33-3.35 (broad t, 1H), 3.52-3.55 (m, 1H), 3.65-3.79 (m, 2H), 3.90-3.94 (m, 0.5H), 4.10-4.14 (m, 0.5H), 4.51-4.56 (d, 1H), 4.65-4.68 (m, 0.5H), 4.72-4.79 (m, 1H), 4.81-4.86 (m, 0.5H), 6.16-6.19 (broad m, 1H), 7.04-7.14 (dd, 1H), 7.26-7.29 (broad t, 1H), 7.34-7.41 (m, 5H), 7.74-7.77 (m, 1H), 8.86-8.90 (m, 1H).

EXAMPLE 52

N-benzyl-N-butyl-N'-{(3R)-1-[(6-methylpyridin-3-yl)carbonyl]pyrrolidin-3-yl}urea The procedure described in example 1 was used but substituting N-benzyl-N-butylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt: MS showed (M+H)$^+$ @ 393; NMR (d$_6$DMSO), 0.76-0.77 (d, 3H), 1.07-1.14 (m, 2H), 1.50-1.55 (m, 2H), 1.97-2.03 (m, 1H), 2.09-2.16 (m, 1H), 2.52 (s, 3H), 3.32-3.3.48 (m, 31H), 3.61-3.64 (m, 0.5H), 3.68-3.74 (m, 0.5H), 3.83-3.86 (m, 1H), 3.95-3.98 (t, 0.5H), 4.17-4.21 (q, 0.5H), 4.67-4.73 (m, 2H), 4.77-4.83 (m, 1H), 6.61 (broad s, 1H), 7.29-7.40 (m, 5H), 7.76-7.78 (d, 1H), 8.86-8.90 (m, 1H).

EXAMPLE 53

N,N-dibenzyl-N'-{(3R)-1-[(6-methylpyridin-3-yl)carbonyl]pyrrolidin-3-yl}urea

The procedure described in example 1 was used but substituting N,N-dibenzylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt: MS showed (M+H)$^+$ @ 429; NMR (d$_6$DMSO): 1.93-1.94 (m, 1H), 2.07-2.14 (m, 1H), 2.52 (s, 3H), 3.38-3.39 (d, 1H), 3.59-3.62 (m, 0.5H), 3.67-3.72 (m, 0.5H), 3.76-3.85 (m, 1H), 3.95-3.98 (t, 1H), 4.15-4.19 (q, 1H), 4.64-4.67 (d, 2H), 4.83 (d, 1H), 6.82 (s, 1H), 7.06-7.13 (dd, 1H), 7.29-7.34 (m, 10H), 7.73-7.77 (t, 1H), 8.83-8.90 (d, 1H).

EXAMPLE 54

N-benzyl-N'-{(3R)-1-[(6-methylpyridin-3-yl)carbonyl]pyrrolidin-3-yl}-N-(2-phenylethyl)urea The procedure described in example 1 was used but substituting N-benzyl-N-(2-phenylethyl)amine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt: MS showed (M+H)$^+$ @ 443; NMR (d$_6$DMSO): 1.88-1.95 (m, 1H), 2.05-2.13 (m, 1H), 2.52 (s, 3H), 2.91-2.98 (m, 2H), 3.38-3.54 (m, 1H), 3.64-3.74 (m, 2H), 3.77-3.85 (m, 1H), 3.92-3.96 (q, 1H), 4.15-4.18 (q, 1H), 4.60-4.76 (m, 3H), 6.43-6.49 (dd, 1H), 7.07-7.13 (dd, 1H), 7.19-7.36 (m, 10H), 7.77-7.80 (t, 1H), 8.86-8.92 (d, 1H).

EXAMPLE 55

N$^3$,N$^3$-diethyl-N$^1$-{(3R)-1-[(6-methylpyridin-3-yl)carbonyl]pyrrolidin-3-yl}piperidine-1,3-dicarboxamide The procedure described in example 1 was used but substituting N,N-diethylpiperidine-3-carboxamide for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt: MS showed (M+H)⁺ @ 416; NMR (d₆DMSO): 0.98-1.04 (m, 6H), 1.22-1.25 (m, 1H), 1.47-1.54 (m, 1H), 1.84-1.94 (m, 1H), 2.00-2.07 (m, 1H), 2.11-2.19 (m, 1H), 2.52 (s, 3H), 2.74-2.89 (m, 3H), 3.17-3.43 (m, 6H), 3.52-3.62 (m, 1H), 3.72-3.75 (m, 0.5H), 3.85-3.93 (m, 1H), 3.97-4.03 (m, 0.5H), 4.20-4.27 (m, 1H), 4.35-4.37 (d, 0.5H), 4.54-4.57 (d, 0.5H), 4.62-4.70 (m, 1H), 6.75 (broad m, 1H), 7.04-7.13 (dd, 1H), 7.77-7.79 (d, 1H), 8.85-8.90 (m, 1H).

EXAMPLE 56

N-{(3R)-1-[(6-methylpyridin-3-yl)carbonyl]pyrrolidin-3-yl}-4-(2-oxo-2,3-dihydro-1H-benzimidazol-1-yl)piperidine-1-carboxamide The procedure described in example 1 was used but substituting 1-piperidin-4-yl-1,3-dihydro-2H-benzimidazol-2-one for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt: MS showed (M+H)⁺ @ 449; NMR (d₆DMSO): 1.03-1.06 (d, 2H), 1.25-1.30 (m, 1H), 1.62-1.70 (m, 1H), 1.85-1.97 (m, 1H), 2.06-2.23 (m, 1H), 2.51-2.52 (d, 3H), 2.75-2.85 (m, 1H), 3.43-3.75 (m, 2H), 4.09-4.21 (m, 3H), 6.33-6.39 (m, 1H), 6.94-6.96 (m, 4H), 7.09-7.14 (m, 1H), 7.75-7.81 (m, 1H), 8.55-8.58 (m, 1H).

EXAMPLE 57

4-ethyl-N-{(3R)-1-[(6-methylpyridin-3-yl)carbonyl]pyrrolidin-3-yl}piperazine-1-carboxamide The procedure described in example 1 was used but substituting 1-ethylpiperazine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the bis-TFA salt:

MS showed (M+H)⁺ @ 346; NMR (d₆DMSO): 0.94-0.97 (m, 3H), 2.01-2.07 (m, 1H), 2.11-2.24 (m, 1H), 2.19-2.41 (m, 4H), 2.52 (s, 3H), 2.64-2.66 (m, 2H), 2.97-3.02 (m, 1H), 3.36-3.38 (m, 2H), 3.39-3.69 (m, 4H), 3.85-3.92 (m, 1H), 3.99-4.02 (m, 0.5H), 4.18-4.24 (m, 0.5H), 7.04-7.07 (m, 1H), 7.37-7.41 (d, 1H), 7.73-7.79 (m, 1H).

EXAMPLE 58

4-benzyl-N-{(3R)-1-[(6-methylpyridin-3-yl)carbonyl]pyrrolidin-3-yl}piperazine-1-carboxamide The procedure described in example 1 was used but substituting 1-benzylpiperazine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the bis-TFA salt:

MS showed (M+H)⁺ @ 408; NMR (d₆DMSO): 1.99-2.04 (m, 1H), 2.11-2.18 (m, 1H), 2.36-2.39 (m, 4H), 2.52 (s, 1H), 3.42-3.44 (m, 3H), 3.52-3.65 (m, 6H), 3.69-3.76 (m, 1H), 3.82-3.91 (m, 1H), 3.98-4.01 (m, 0.5H), 4.19-4.22 (m, 0.5H), 4.61-4.65 (m, 0.5H), 4.72-4.76 (m, 0.5H), 6.99-7.12 (m, 2H), 7.26-7.41 (m, 5H), 7.77-7.79 (d, 1H), 8.86-8.90 (d, 1H).

EXAMPLE 59

N-methyl-N'-{(3R)-1-[(6-methylpyridin-3-yl)carbonyl]pyrrolidin-3-yl}-N-propylurea The procedure described in example 1 was used but substituting N-methyl-N-propylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt: MS showed (M+H)⁺ @ 305; NMR (d₆DMSO): 0.75-0.80 (t, 3H), 1.43-1.55 (m, 2H), 1.88-1.99 (m, 1H), 2.08-2.19 (m, 1H), 2.49 (s, 3H), 3.23-3.28 (t, 2H), 3.50-3.79 (broad m, 2H), 3.93-4.03 (broad m, 1H), 5.80-5.87 (broad m, 1H), 7.03-7.06 (d, 1H), 7.71-7.75 (dd, 1H), 8.81-8.82 (d, 1H).

EXAMPLE 60

N-isobutyl-N-methyl-N'-{(3R)-1-[(6-methylpyridin-3-yl)carbonyl]pyrrolidin-3-yl}urea The procedure described in example 1 was used but substituting N-isobutyl-N-methylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt: MS showed (M+H)⁺ @ 319; NMR (d₆DMSO): 0.81-0.84 (d, 6H), 1.84-1.99 (m, 2H), 2.08-2.19 (m, 1H), 2.49 (s, 3H), 2.85 (s, 3H), 3.13-3.15 (d, 2H), 3.50-3.79 (broad m, 3H), 3.94-4.04 (broad m, 1H), 5.75-5.84 (broad m, 1H), 7.03-7.06 (d, 1H), 7.72-7.75 (dd, 1H), 8.82-8.83 (d, 1H).

EXAMPLE 61

N-methyl-N-(3-methylbutyl)-N'-{(3R)-1-[(6-methylpyridin-3-yl)carbonyl]pyrrolidin-3-yl}urea The procedure described in example 1 was used but substituting N-methyl-N-(3-methylbutyl)amine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt: MS showed (M+H)⁺ @ 333; NMR (d₆DMSO): 0.84-0.86 (d, 6H), 1.37-1.54 (m, 3H), 1.89-2.00 (m, 3H), 2.07-2.20 (m, 1H), 2.07-2.20 (m, 1H), 2.49 (s, 3H), 2.84 (s, 3H), 3.32-3.37 (t, 2H), 3.50-3.79 (broad m, 3H), 3.93-4.04 (broad m, 1H), 4.52-4.59 (broad m, 1H), 5.78-5.85 (broad m, 1H), 7.04-7.06 (d, 1H), 7.72-7.75 (dd, 1H), 8.82-8.83 (d, 1H).

EXAMPLE 62

N-methyl-N'-{(3R)-1-[(6-methylpyridin-3-yl)carbonyl]pyrrolidin-3-yl}-N-prop-2-ynylurea The procedure described in example 1 was used but substituting N-methyl-N-prop-2-ynylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt: MS showed (M+H)+ @ 301; NMR (d$_6$DMSO): 1.87-1.99 (m, 1H), 2.07-2.17 (m, 1H), 2.49 (s, 3H), 2.74-2.76 (t, 1H), 2.94 (s, 3H), 3.50-3.76 (broad m, 3H), 3.92-4.02 (broad m, 1H), 4.25-4.26 (d, 1H), 4.51-4.58 (broad s, 1H), 6.20-6.28 (broad s, 1H), 7.03-7.06 (d, 1H), 7.70-7.73 (dd, 1H), 8.80-8.81 (d, 1H).

EXAMPLE 63

N-ethyl-N'-{(3R)-1-[(6-methylpyridin-3-yl)carbonyl]pyrrolidin-3-yl}-N-propylurea The procedure described in example 1 was used but substituting N-ethyl-N-propylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt: MS showed (M+H)+ @ 319; NMR (d$_6$DMSO): 0.76-0.81 (t, 3H), 1.04-1.09 (t, 3H), 1.47-1.59 (m, 2H), 1.88-1.99 (m, 1H), 2.07-2.19 (m, 1H), 2.49 (s, 3H), 3.20-3.34 (m, 4H), 3.49-3.78 (broad m, 2H), 3.92-4.03 (broad s, 1H), 4.53-4.63 (broad s, 1H), 5.70-5.78 (broad s, 1H), 7.03-7.06 (d, 1H), 7.71-7.75 (dd, 1H), 8.82-8.83 (d, 1H).

EXAMPLE 64

N-isopropyl-N'-{(3R)-1-[(6-methylpyridin-3-yl)carbonyl]pyrrolidin-3-yl}-N-propylurea The procedure described in example 1 was used but substituting N-isopropyl-N-propylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt: MS showed (M+H)+ @ 333; NMR (d$_6$DMSO): 0.77-0.82 (t, 3H), 1.08-1.10 (d, 6H), 1.12-1.15 (d, 1H), 1.56-1.66 (m, 2H), 1.88-1.99 (m, 1H), 2.09-2.19 (m, 1H), 2.49 (s, 3H), 3.07-3.12 (t, 2H), 3.51-3.78 (broad m, 2H), 3.94-4.03 (broad m, 1H), 4.31-4.41 (m, 1H), 4.55-4.62 (broad m, 1H), 7.03-7.08 (d, 1H), 7.72-7.75 (dd, 1H), 8.82-8.83 (d, 1H).

EXAMPLE 65

N-(sec-butyl)-N'-{(3R)-1-[(6-methylpyridin-3-yl)carbonyl]pyrrolidin-3-yl}-N-propylurea The procedure described in example 1 was used but substituting N-(sec-butyl)-N-propylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt: MS showed (M+H)+ @ 347; NMR (d$_6$DMSO): 0.78-0.84 (m, 6H), 1.07-1.09 (d, 3H), 1.33-1.42 (m, 1H), 1.48-1.66 (m, 3H), 1.88-2.00 (m, 1H), 2.07-2.19 (m, 1H), 2.49 (s, 3H), 2.97-3.18 (m, 2H), 3.49-3.78 (broad m, 4H), 3.91-4.03 (broad m, 1H), 4.05-4.12 (q, 1H), 4.51-4.60 (m, 2H), 5.57-5.66 (broad m, 1H), 7.03-7.06 (d, 1H), 7.72-7.75 (dd, 1H), 8.83 (d, 1H).

EXAMPLE 66

N,N-dibutyl-N'-{(3R)-1-[(6-methylpyridin-3-yl)carbonyl]pyrrolidin-3-yl}urea

The procedure described in example 1 was used but substituting N,N-dibutylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt: MS showed (M+H)+ @ 361; NMR (d$_6$DMSO): 0.83-0.88 (t, 6H), 1.18-1.30 (m, 4H), 1.50-1.59 (m, 4H), 1.89-2.01 (m, 1H), 2.09-2.20 (m, 1H), 2.49 (s, 3H), 3.27-3.32 (t, 4H), 3.50-3.79 (m, 2H), 3.95-4.03 (m, 1H), 4.54-4.61 (m, 1H), 5.67-5.74 (m, 1H), 7.04-7.06 (d, 1H), 7.72-7.75 (dd, 1H), 8.82-8.83 (d, 1H).

EXAMPLE 67

N-(2-cyanoethyl)-N-cyclopropyl-N'-{(3R)-1-[(6-methylpyridin-3-yl)carbonyl]pyrrolidin-3-yl}urea The procedure described in example 1 was used but substituting 3-(cyclopropylamino)propanenitrile for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt: MS showed (M+H)+ @ 341; NMR (d$_6$DMSO): 0.71-0.73 (m, 4H), 1.87-1.98 (m, 1H), 2.07-2.19 (m, 1H), 2.50 (s, 3H), 2.54-2.61 (m, 1H), 2.68-2.72 (m, 2H), 3.54-3.76 (m, 4H), 3.92-3.98 (m, 1H), 4.49-4.55 (m, 1H), 5.90-5.96 (m, 1H), 7.06-7.09 (d, 1H), 7.76-7.79 (dd, 1H), 8.85-8.86 (d, 1H).

EXAMPLE 68

2-ethyl-N-{(3R)-1-[(6-methylpyridin-3-yl)carbonyl]pyrrolidin-3-yl}piperidine-1-carboxamide The procedure described in example 1 was used but substituting 2-ethylpiperidine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt: MS showed (M+H)+ @ 343; NMR (d$_6$DMSO): 0.78-0.83 (m, 3H), 1.29-1.52 (m, 6H), 1.58-1.76 (m, 1H), 1.89-2.02 (m, 1H), 2.09-2.21 (m, 1H), 2.49 (s, 3H), 2.74-2.83 (m, 1H), 3.52-3.78 (broad m, 3H), 3.97-4.03 (m, 2H), 4.21-4.27 (m, 1H), 4.56-4.64 (m, 1H), 5.96-6.06 (m, 1H), 7.03-7.06 (d, 1H), 7.71-7.75 (m, 1H), 8.81-8.83 (m, 1H).

EXAMPLE 69

N-{(3R)-1-[(6-methylpyridin-3-yl)carbonyl]pyrrolidin-3-yl}-4-propylpiperidine-1-carboxamide The procedure described in example 1 was used but substituting 4-propylpiperidine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt: MS showed (M+H)+ @ 359; NMR (d$_6$DMSO): 0.79-0.84 (t, 3H), 0.97-1.12 (m, 4H), 1.15-1.32 (m, 3H), 1.48-1.52 (dd, 2H), 1.91-2.02 (m, 1H), 2.10-2.21 (m, 1H), 2.49 (s, 3H), 2.68 (m, 2H), 3.50-3.80 (broad m, 3H), 3.98-4.05 (broad m, 1H), 4.13-4.17 (m, 2H), 4.56-4.65 (m, 1H); 7.03-7.06 (d, 1H0, 7.71-7.75 (dd, 1H), 8.82-8.83 (d, 1H).

EXAMPLE 70

N-{(3R)-1-[(6-methylpyridin-3-yl)carbonyl]pyrrolidin-3-yl}azepane-1-carboxamide

The procedure described in example 1 was used but substituting azepane for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt: MS showed (M+H)$^+$ @ 331; NMR (d$_6$DMSO): 1.41-1.48 (m, 4H), 1.56-1.64 (m, 4H), 1.89-2.00 (m, 1H), 2.09-2.20 (m, 1H), 2.49 (s, 3H), 3.39-3.48 (m, 5H), 3.50-3.79 (broad m, 2H), 3.96-4.05 (broad m, 1H), 4.55-4.64 (broad m, 1H), 7.03-7.06 (d, 1H), 7.72-7.75 (dd, 1H), 8.82-8.83 (d, 1H).

EXAMPLE 71

N-ethyl-N-(2-methoxyethyl)-N'-{(3R)-1-[(6-methylpyridin-3-yl)carbonyl]pyrrolidin-3-yl}urea The procedure described in example 1 was used but substituting N-ethyl-N-(2-methoxyethyl)amine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt: MS showed (M+H)$^+$ @ 335; NMR (d$_6$DMSO): 1.04-1.09 (t, 3H), 1.84-1.97 (m, 1H), 2.05-2.16 (m, 1H), 2.49 (s, 3H), 3.24 (s, 3H), 3.34-3.47 (m, 6H), 3.50-3.79 (m, 3H), 3.51-3.79 (m, 3H), 3.87-3.99 (m, 1H), 4.47-4.55 (m, 1H), 6.01-6.08 (broad m, 1H), 7.05-7.07 (d, 1H), 7.74-7.77 (dd, 1H), 8.85-8.86 (d, 1H).

EXAMPLE 72

N-(2-methoxyethyl)-N'-{(3R)-1-[(6-methylpyridin-3-yl)carbonyl]pyrrolidin-3-yl}-N-propylurea The procedure described in example 1 was used but substituting N-(2-methoxyethyl)-N-propylamine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt: MS showed (M+H)$^+$ @ 349; NMR (d$_6$DMSO): 0.77-0.82 (t, 3H), 1.49-1.61 (m, 2H), 1.84-1.97 (m, 1H), 2.05-2.16 (m, 1H), 2.49 (s, 3H), 3.29-3.34 (t, 2H), 3.40-3.49 (m, 4H), 3.52-3.77 (broad m, 3H), 3.87-3.98 (broad m, 1H), 4.48-4.54 (m, 1H), 6.03-6.09 (m, 1H), 7.05-7.07 (m, 1H), 7.74-7.78 (dd, 1H), 8.85-8.86 (d, 1H).

EXAMPLE 73

N,N-bis(2-methoxyethyl)-N'-{(3R)-1-[(6-methylpyridin-3-yl)carbonyl]pyrrolidin-3-yl}urea The procedure described in example 1 was used but substituting N,N-bis(2-methoxyethyl)amine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt: MS showed (M+H)$^+$ @ 365; NMR (d$_6$DMSO): 1.81-1.92 (m, 1H), 2.03-2.15 (m, 1H), 2.50 (s, 3H), 3.24 (s, 6H), 3.47-3.77 (m, 1H), 3.85-3.97 (m, 1H), 4.42-4.52 (m, 1H), 6.22-6.28 (broad m, 1H), 7.05-7.08 9 d, 1H), 7.76-7.79 (dd, 1H), 8.86-8.87 (d, 1H).

EXAMPLE 74

1,3,3-trimethyl-N-{(3R)-1-[(6-methylpyridin-3-yl)carbonyl]pyrrolidin-3-yl}-6-azabicyclo[3.2.1]octane-6-carboxamide The procedure described in example 1 was used but substituting 1,3,3-trimethyl-6-azabicyclo[3.2.1]octane for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt: MS showed (M+H)$^+$ @ 385; NMR (d$_6$DMSO): 0.85-0.86 (d, 3H), 0.90 (s, 3H), 1.02-1.03 (d, 3H), 1.11-1.19 (t, 2H), 1.26-1.40 (q, 2H), 1.50-1.57 (m, 1H), 1.92-2.07 (m, 2H), 2.10-2.21 (m, 1H), 2.49 (s, 3H), 2.97-3.00 (dd, 1H), 3.27-3.32 (d, 1H), 3.52-3.83 (m, 2H), 3.95-4.06 (m, 1H), 4.28-4.32 (m, 1H), 4.57-4.66 (broad m, 1H), 7.04-7.07 (d, 1H), 7.73-7.77 (dd, 1H), 8.84-8.85 (d, 1H).

EXAMPLE 75

N-methyl-N'-{(3R)-1-[(6-methylpyridin-3-yl)carbonyl]pyrrolidin-3-yl}-N-(2-phenylethyl)urea The procedure described in example 1 was used but substituting N-methyl-N-(2-phenylethyl)amine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 367; NMR (d$_6$DMSO): 1.76-1.83 (m, 0.5H), 1.86-1.92 (m, 0.5H), 1.96-2.09 (m, 1H), 2.51 (s, 3H), 2.66-2.63 (m, 1H), 2.72 (s, 3H); 2.78 (s, 1H), 3.18 (m, 1H), 3.38-3.52 (m, 3H), 3.60-3.68 (m, 2H), 4.02-4.06 (m, 0.5H), 4.18-4.23 (m, 0.5H), 6.17-6.25 (dd, 1H), 7.16-7.34 (m, 5H), 7.79-7.83 (m, 1H), 8.57-8.59 (d, 1H).

EXAMPLE 76

4-sec-butyl-N-{(3R)-1-[(6-methylpyridin-3-yl)carbonyl]pyrrolidin-3-yl}piperazine-1-carboxamide The procedure described in example 1 was used but substituting 1-sec-butylpiperazine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 374; NMR (d$_6$DMSO): 0.82-0.90 (m, 6H), 1.20-1.28 (m, 1H), 1.43-1.51 (m, 1H), 1.75-1.92 (m, 1H), 1.98-2.10 (m, 1H), 2.26-2.43 (m, 5H), 2.50 (s, 3H), 3.21-3.23 (m, 3H), 3.44-3.54 (m, 3H); 3.59-3.69 (m, 2H), 4.04-4.07 (m, 0.5H), 4.19-4.23 (m, 0.5H), 6.45-6.51 (dd, 1H), 7.31-7.33 (d, 1H), 8.57-8.60 (d, 1H).

EXAMPLE 77

4-(2-ethoxyethyl)-N-{(3R)-1-[(6-methylpyridin-3-yl)carbonyl]pyrrolidin-3-yl}piperazine-1-carboxamide The procedure described in example 1 was used but substituting 1-(2-ethoxyethyl)piperazine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 390; NMR (d$_6$DMSO): 1.07-1.11 (m, 3H), 1.75-1.93 (m, 1H), 1.98-2.10 (m, 1H), 2.31-2.37 (m, 4H), 2.50 (s, 3H), 3.21-3.23 (m, 3H), 3.38-3.42 (m, 3H), 3.43-3.49 (m, 4H), 3.61-3.69 (m, 1H), 4.04-4.07 (m, 0.5H), 4.19-4.23 (m, 0.5H), 6.47-6.53 (dd, 1H), 7.31-7.33 (d, 1H)), 7.79-7.83 (m, 1H), 8.57-8.60 (d, 1H).

EXAMPLE 78

4-cyclohexyl-N-{(3R)-1-[(6-methylpyridin-3-yl)carbonyl]pyrrolidin-3-yl}piperazine-1-carboxamide The procedure described in example 1 was used but substituting 1-cyclohexylpiperazine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 400; NMR (d$_6$DMSO): 1.02-1.24 (m, 6H), 1.55-1.57 (d, 1H), 1.71-1.73 (m, 4H), 1.99-2.09 (m, 1H), 2.17-2.22 (broad m, 1H), 2.37-2.43 (m, 4H), 2.50 (s, 3H), 3.20-3.28 (m, 4H), 3.31-3.34 (dd, 1H), 3.44-3.69 (m, 2H), 4.03-4.07 (m, 1H), 4.19-4.22 (m, 1H), 6.46-6.51 (dd, 1H), 7.31-7.33 (m, 1H), 7.79-7.83 (m, 1H), 8.57-8.59 (m, 1H).

EXAMPLE 79

N-{(3R)-1-[(6-methylpyridin-3-yl)carbonyl]pyrrolidin-3-yl}-4-(2-thien-2-ylethyl)piperazine-1-carboxamide The procedure described in example 1 was used but substituting 1-(2-thien-2-ylethyl)piperazine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M–H)$^+$ @ 426; NMR (d$_6$DMSO): 1.79-1.92 (m, 1H); 1.98-2.11 (m, 1H), 2.34-2.41 (m, 5H), 2.50 (s, 3H), 2.52-2.60 (m, 2H), 2.93-2.98 (m, 3H), 3.23-3.28 (m, 2H), 3.43-3.54 (m, 2H), 3.60-3.70 (m, 2H), 4.05-4.08 (m, 0.5H), 4.20-4.24 (m, 0.5H), 6.50-6.55 (dd, 1H), 6.87-6.89 (m, 1H), 6.91-6.94 (m, 1H), 7.29-7.33 (m, 2H), 7.79-7.84 (m, 1H).

EXAMPLE 80

N-{(3R)-1-[(6-methylpyridin-3-yl)carbonyl]pyrrolidin-3-yl}-4-(2-oxo-2-piperidin-1-ylethyl)piperazine-1-carboxamide The procedure described in example 1 was used but substituting 1-(2-oxo-2-piperidin-1-ylethyl)piperazine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M–H)$^+$ @ 443; NMR (d$_6$DMSO): 1.41-1.58 (m, 8H), 1.77-1.93 (m, 2H), 1.98-2.10 (m, 1H), 2.31-2.37 (m, 5H), 2.50 (s, 3H), 3.11-3.13 (d, 2H), 3.24 (broad s, 2H), 3.39-3.45 (broad s, 4H), 3.58-3.70 (m, 2H), 4.03-4.08 (m, 0.5H), 4.19-4.23 (m, 0.5H), 6.49-6.55 (dd, 1H), 7.31-7.33 (d, 1H), 7.79-7.83 (t, 1H), 8.57-8.60 (d, 1H).

EXAMPLE 81

4-(cyclohexylcarbonyl)-N-{(3R)-1-[(6-methylpyridin-3-yl)carbonyl]pyrrolidin-3-yl}piperazine-1-carboxamide The procedure described in example 1 was used but substituting 1-(cyclohexylcarbonyl)piperazine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M–H)$^+$ @ 426; NMR (d$_6$DMSO): 1.10-1.19 (m, 1H), 1.24-1.34 (m, 4H), 1.58-1.69 (m, 6H), 1.78-1.93 (m, 1H), 1.99-2.11 (m, 1H), 2.50 (s, 3H), 2.53-2.64 (m, 1H), 3.22-3.24 (m, 4H), 3.41-3.55 (m, 6H), 3.60-3.71 9 m, 1H), 4.06-4.10 (m, 0.5H), 6.59-6.64 (dd, 1H), 7.31-7.33 (d, 1H), 7.79-7.84 (t, 1H), 8.57-8.60 (d, 1H).

EXAMPLE 82

N-benzyl-N-(2-hydroxyethyl)-N'-{(3R)-1-[(6-methylpyridin-3-yl)carbonyl]pyrrolidin-3-yl}urea The procedure described in example 1 was used but substituting 2-(benzylamino)ethanol for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M–H)$^+$ @ 383; NMR (d$_6$DMSO): 1.79-1.91 (m, 2H), 1.99-2.13 (m, 1H), 2.51 (s, 3H), 3.16-3.24 (m, 2H), 3.41-3.51 (m, 3H), 3.57-3.69 (m, 2H), 4.09-4.14 (m, 0.5H), 4.23-4.26 (m, 0.5H), 4.44-4.50 (d, 2H), 4.90-5.02 (m, 1H), 6.52-6.58 (dd, 1H), 7.14-7.15 (d, 1H), 7.21-7.35 (m, 5H), 7.78-7.78-7.80 (d, 1H), 8.57 (s, 1H).

EXAMPLE 83

N-(2-hydroxy-2-phenylethyl)-N-methyl-N'-{1-[(6-methylpyridin-3-yl)carbonyl]pyrrolidin-3-yl}urea The procedure described in example 1 was used but substituting 2-(methylamino)-1-phenylethanol for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed $(M+H)^+$ @ 383; NMR ($d_6$DMSO): 1.75-1.91 (m, 1H), 1.98-2.09 (m, 1H), 2.50 (m, 3H), 2.70-2.76 9 d, 3H), 3.18-3.24 (m, 1H), 3.44-3.54 (m, 2H), 3.59-3.69 (m, 2H), 4.03-4.06 (m, 0.5H), 4.18-4.21 (m, 0.5H), 4.69-4.75 (d, 1H), 5.55-5.62 (d, 1H), 6.24-6.33 (dt, 1H), 7.20-7.26 (m, 1H), 7.29-7.36 (m, 5H); 7.80-7.84 (t, 1H), 8:58-8.60 (d, 1H).

EXAMPLE 84

N-methyl-N'-{(3R)-1-[(6-methylpyridin-3-yl)carbonyl]pyrrolidin-3-yl}-N-(2-pyridin-2-ylethyl)urea The procedure described in example 1 was used but substituting N-methyl-N-(2-pyridin-2-ylethyl)amine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed $(M-H)^+$ @ 368; NMR ($d_6$DMSO): 1.78-1.91 (m, 1H), 1.96-2.09 (m, 1H), 2.49 (s, 3H), 2.71-2.77 (d, 3H), 2.83-2.86 (t, 1H), 2.90-2.92 (t, 1H), 3.17-3.21 (m, 1H); 3.43-3.68 (m, 5H), 4.01-4.05 (m, 0.5H), 4.17-4.20 (m, 0.5H), 6.26-6.33 (dd, 1H), 7.17-7.28 (m, 2H), 7.32-7.34 (dd, 1H), 7.64-7.72 (m, 1H), 7.79-7.83 (t, 1H), 8.45-8.49 (dd, 1H), 8.57-8.60 (d, 1H).

EXAMPLE 85

4-hydroxy-N-{(3R)-1-[(6-methylpyridin-3-yl)carbonyl]pyrrolidin-3-yl}piperidine-1-carboxamide The procedure described in example 1 was used but substituting 4-hydroxypiperidine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed $(M-H)^+$ @ 331; NMR ($d_6$DMSO): 1.15-1.27 (m, 2H), 1.61-1.69 (m, 2H), 1.75-1.93 (m, 1H), 1.99-2.10 (m, 1H), 2.50 (s, 3H), 2.82-2.91 (m, 2H); 3.21-3.24 (m, 1H), 3.41-3.72 (m, 6H), 4.03-4.07 (m, 0.5H), 4.18-4.22 (m, 0.5H), 6.64 (broad m, 1H); 6.44-6.50 (dd, 1H), 7.31-7.33 (d, 1H), 7.79-7.83 (t, 1H), 8.57-8.60 (d, 1H).

EXAMPLE 86

$N^1$-{(3R)-1-[(6-methylpyridin-3-yl)carbonyl]pyrrolidin-3-yl}piperidine-1,4-dicarboxamide The procedure described in example 1 was used but substituting piperidine-4-carboxamide for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed $(M+H)^+$ @ 360; NMR ($d_6$DMSO): 1.29-1.42 (m, 2H), 1.61-1.67 (broad m, 2H), 1.78-1.92 (m, 1H), 1.98-2.10 (m, 1H), 2.17-2.27 (m, 1H), 2.50 (s, 3H), 2.59-2.69 (m, 2H), 3.21-3.25 (m, 1H), 3.42-3.55 (m, 1H), 3.59-3.70 (m, 2H), 3.89-3.92 (broad d, 1H), 3.96-3.99 (broad d, 1H): 4.04-4.08 (m, 0.5H), 4.19-4.23 (m, 0.5H), 6.45-6.51 (dd, 1H), 6.57-6.76 (d, 1H), 7.22-7.24 (d, 1H), 7.31-7.33 (d, 1H), 7.79-7.84 (t, 1H), 8.57-86.0 (d, 1H).

EXAMPLE 87

N-{(3R)-1-[(6-methylpyridin-3-yl)carbonyl]pyrrolidin-3-yl}-1,4-dioxa-8-azaspiro[4.5]decane-8-carboxamide The procedure described in example 1 was used but substituting 1,4-dioxa-8-azaspiro[4.5]decane for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed $(M+H)^+$ @ 375; NMR ($d_6$DMSO): 1.48-1.55 (dt, 4H), 1.77-1.92 (m, 1H), 1.98-2.10 (m, 1H), 2.50 (s, 3H), 3.21-3.25 (m, 1H), 3.36-3.39 (m, 3H), 3.43-3.54 (m, 2H), 3.59-3.69 (m, 2H), 3.87-3.89 (d, 4H), 4.04-4.07 (m, 0.5H), 4.19-4.22 (m, 0.5H), 6.54-6.60 (dd, 1H), 7.31-7.33 (d, 1H), 7.79-7.83 (m, 1H), 8.57-8.59 (dd, 1H).

EXAMPLE 88

2,6-dimethyl-N-{(3R)-1-[(6-methylpyridin-3-yl)carbonyl]pyrrolidin-3-yl}morpholine-4-carboxamide The procedure described in example 1 was used but substituting 2,6-dimethylmorpholine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed $(M+H)^+$ @ 347; NMR ($d_6$DMSO): 1.04-1.05 (d, 3H), 1.07-1.08 (d, 3H), 1.79-1.92 (m, 1H), 1.98-2.12 (m, 1H), 2.23-2.34 (m, 1H), 2.50 (s, 3H), 2.94-3.04 (m, 1H), 3.21-3.24 (m, 2H), 3.46-3.55 (m, 2H), 3.60-3.71 (m, 2H), 3.76-3.78 (d, 1H), 3.83-3.86 (d, 1H), 4.06-4.10 (m, 0.5H), 4.20-4.24 (m, 0.5H), 6.49-6.55 (dd, 1H), 7.31-7.33 9 d, 1H), 7.79-7.84 (t, 1H), 8.57-8.60 (d, 1H).

EXAMPLE 89

N-{(3R)-1-[(6-methylpyridin-3-yl)carbonyl]pyrrolidin-3-yl}-4-phenylpiperazine-1-carboxamide The procedure described in example 1 was used but substituting 1-phenylpiperazine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 394; NMR (d$_6$DMSO): 1.80-1.95 (m, 1H), 2.00-2.12 (m, 1H), 2.51 (s, 3H), 3.04-3.06 (t, 2H), 3.09-3.11 (t, 2H), 3.24-3.27 (m, 1H), 3.39-3.41 (t, 2H), 3.46-3.48 (t, 2H), 3.49-3.58 (m, 1H), 3.61-3.72 (m, 2H), 4.08-4.11 (m, 0.5H), 4.23-4.26 (m, 0.5H), 6.62-6.68 (dd, 1H), 6.78-6.82 (m, 1H), 6.94-6.98 (t, 2H), 7.20-7.24 (q, 2H), 7.30-7.34 (t, 1H), 7.79-7.84 (qd, 1H), 8.58-8.60 (d, 1H).

EXAMPLE 90

N-{(3R)-1-[(6-methylpyridin-3-yl)carbonyl]pyrrolidin-3-yl}-4-pyridin-2-ylpiperazine-1-carboxamide The procedure described in example 1 was used but substituting 1-pyridin-2-ylpiperazine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 395; NMR (d$_6$DMSO): 1.79-1.84 (m, 0.5H), 1.87-1.93 (m, 0.5H), 1.99-2.10 (m, 1H), 2.49 (s, 3H), 3.40-3.42 (m, 6H), 3.45-3.46 (m, 4H), 3.48-3.57 (m, 1H), 3.60-3.71 (m, 1H), 4.07-4.11 (m, 0.5H), 4.22-4.25 (m, 0.5H), 6.60-6.66 (m, 2H), 6.81-6.85 (t, 1H), 7.29-7.33 (t, 1H), 7.51-7.55 (q, 1H), 7.79-7.83 (q, 1H), 8.09-8.11 (t, 1H), 8.56-8.59 (d, 1H).

EXAMPLE 91

4-(2-fluorophenyl)-N-{(3R)-1-[(6-methylpyridin-3-yl)carbonyl]pyrrolidin-3-yl}piperazine-1-carboxamide The procedure described in example 1 was used but substituting 1-(2-fluorophenyl)piperazine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M–H)$^+$ @ 410; NMR (d$_6$DMSO): 1.77-1.84 (m, 0.5H), 1.86-1.91 (m, 0.5H), 1.97-2.10 (m, 1H), 2.26-2.28 (t, 2H), 2.30-2.32 (t, 2H); 2.49 (s, 3H), 3.20-3.26 (m, 3H), 3.45-3.48 (d, 2H), 3.49-3.55 (m, 1H), 3.59-3.69 (m, 2H), 4.04-4.07 (m, 0.5H), 4.19-4.23 (m, 0.5H), 7.24-7.33 (m, 6H), 7.79-7.83 (m, 1H), 8.57-8.59 (m, 1H).

EXAMPLE 92

4-(4-fluorophenyl)-N-{(3R)-1-[(6-methylpyridin-3-yl)carbonyl]pyrrolidin-3-yl}piperazine-1-carboxamide The procedure described in example 1 was used but substituting 1-(4-fluorophenyl)piperazine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 410; NMR (d$_6$DMSO): 1.81-1.86 (m, 0.5H), 1.88-1.94 (m, 0.5H), 2.00-2.13 (m, 1H), 2.49 (s, 3H), 2.89-2.93 (m, 2H): 2.95-2.97 (t, 2H), 3.41-3.43 (t, 2H), 3.51-3.58 (m, 1H), 3.61-3.72 (m, 2H), 4.08-4.12 (m, 1H), 4.23-4.26 (m, 1H), 6.61-6.67 (dd, 1H), 6.96-7.16 (m, 4H), 7.31-7.34 (dd, 1H), 7.80-7.84 (m, 1H), 8.58-8.61 (d, 1H).

EXAMPLE 93

4-(2-methoxyphenyl)-N-{(3R)-1-[(6-methylpyridin-3-yl)carbonyl]pyrrolidin-3-yl}piperazine-1-carboxamide The procedure described in example 1 was used but substituting 1-(2-methoxyphenyl)piperazine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 424; NMR (d$_6$DMSO): 1.81-1.86 (m, 0.5H), 1.88-1.96 (m, 0.5H), 2.00-2.12 (m, 1H), 2.49 (s, 3H), 2.82-2.95 (m, 5H), 3.44-3.58 (m, 5H), 3.61-3.72 (m, 2H), 3.77-3.79 (d, 3H), 4.07-4.11 (m, 0.5H), 4.23-4.26 (m, 0.5H), 6.56-6.62 (dd, 1H), 6.87-6.90 (m, 2H), 6.93-6.99 (m, 2H), 7.31-7.34 (d, 1H), 7.80-7.84 (t, 1H), 8.58-8.60 (d, 1H).

EXAMPLE 94

4-methyl-N-{(3R)-1-[(6-methylpyridin-3-yl)carbonyl]pyrrolidin-3-yl}-1,4-diazepane-1-carboxamide The procedure described in example 1 was used but substituting 1-methyl-1,4-diazepane for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)$^+$ @ 404; NMR (d$_6$DMSO): 1.68-1.78 (m, 2H), 1.80-1.94 (m, 1H), 1.97-2.10 (m, 1H), 2.21-2.24 (d, 3H): 2.37-2.48 (m, 5H), 2.50 (s, 3H), 3.40-3.58 (m, 5H), 3.61-3.69 (m, 2H), 4.05-4.10 (m, 0.5H), 4.21-4.25 (m, 0.5H), 6.17-6.24 (dd, 1H), 7.31-7.33 (d, 1H).

EXAMPLE 95 ethyl {4-[({(3R)-1-[(6-methylpyridin-3-yl)carbonyl]pyrrolidin-3-yl}amino)carbonyl]piperazin-1-yl}acetate The procedure described in example 1 was used but substituting ethyl piperazin-1-ylacetate for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M+H)+ @ 404; NMR (d$_6$DMSO): 1.16-1.20 (m, 3H), 1.77-1.83 (m, 0.5H), 1.85-1.91 (m, 0.5H), 1.98-2.10 (m, 1H), 2.41-2.43 (t, 2H); 2.45-2.47 (t, 2H), 2.50 (s, 3H), 3.24-3.25 (m, 2H), 3.30-3.31 (m, 2H), 3.43-3.54 (m, 4H), 3.60-3.70 (m, 2H), 4.05-4.11 (m, 2.5H), 4.19-4.23 (m, 0.5H), 6.49-6.55 (dd, 1H), 7.31-7.33 (d, 1H), 7.79-7.83 (m, 1H), 8.57-8.59 (d, 1H).

EXAMPLE 96

N-{(3R)-1-[(6-methylpyridin-3-yl)carbonyl]pyrrolidin-3-yl}-4-(4-nitrophenyl)piperazine-1-carboxamide The procedure described in example 1 was used but substituting 1-(4-nitrophenyl)piperazine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M-H)+ @ 437; NMR (d$_6$DMSO): 1.82-1.87 (m, 0.5H), 1.87-1.95 (m, 0.5H), 1.91 (s, 2H), 2.00-2.13 (m, 1H), 2.50 (s, 3H), 2.84 (m, 4H), 3.53-3.72 (m, 7H), 4.07-4.12 (m, 0.5H), 4.23-4.28 (m, 0.5H), 6.64-6.70 (dd, 1H), 7.00-7.05 (m, 2H), 7.31-7.34 (t, 1H), 7.80-7.84 (t, 1H), 8.04-8.08 (m, 2H), 8.58-8.60 (d, 1H).

EXAMPLE 97

3-(methoxymethyl)-N-{(3R)-1-[(6-methylpyridin-3-yl)carbonyl]pyrrolidin-3-yl}piperidine-1-carboxamide The procedure described in example 1 was used but substituting 3-methoxymethylpiperidine for benzylamine. After workup the crude product was purified by HPLC using C-18 column and a solvent mixture varying in a gradient of 10% to 90% acetonitrile/water containing 0.1% TFA. The pure fractions were lyophilized to yield the title compound as the TFA salt. This was dissolved in methylene chloride and shaken with a MP-carbonate resin to yield the desired product as the free base: MS showed (M-H)+ @ 361; NMR (d$_6$DMSO): 1.06-1.17 (m, 0.5H), 1.23-1.37 (m, 3H), 1.77-1.84 (m, 0.5H), 1.85-1.92 (m, 0.5H), 1.96-2.10 (m, 1H), 2.37-2.47 (m, 1H), 2.51 (s, 3H), 2.61-2.71 (m, 1H), 3.13-3.19 (m, 2H), 3.21-3.23 (d, 3H), 3.42-3.55 (m, 1H), 3.60-3.69 (m, 1H), 3.74-3.94 (m, 2H), 4.03-4.17 (m, 0.5H), 4.18-4.22 (m, 0.5H), 6.42-6.48 (dd, 1H), 7.31-7.33 (d, 1H), 7.79-7.83 (t, 1H), 8.56-8.59 (d, 1H).

It will be evident to one skilled in the art that the present invention is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (I)

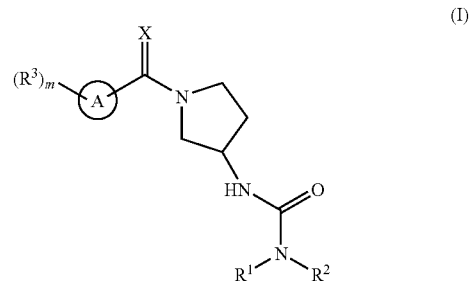

or a therapeutically acceptable salt thereof, wherein

A is selected from the group consisting of pyridazinyl, pyridinyl, pyridine N-oxide, pyrimidinyl, indol-3-yl, pyrazol-4-yl, pyrazinyl, isoxazol-4-yl, and triazinyl;

$R^1$ and $R^2$ are independently selected from the group consisting of hydrogen, alkenyl, alkoxy, alkoxyalkyl, alkyl, alkynyl, aryl, arylalkyl, cyanoalkyl, cycloalkyl, (cycloalkyl)alkyl, haloalkyl, heterocyclyl, heterocyclylalkyl, hydroxyalkyl, $(NR^AR^B)$alkyl, and $(NR^AR^B)$carbonyl; or $R^1$ and $R^2$, together with the nitrogen atom to which they are attached, form a five- to seven-membered ring containing zero or one additional heteroatom selected from the group consisting of nitrogen, oxygen, and sulfur, wherein the remaining atoms are carbon; wherein the ring can be optionally substituted with one, two, three, or four substituents independently selected from the group consisting of alkoxy, alkoxyalkyl, alkoxycarbonyl, alkoxycarbonylalkyl, alkyl, alkylene, alkylcarbonyl, alkylsulfanylalkyl, aryl, arylalkyl, arylcarbonyl, arylcarbonylalkyl, cycloalkyl, (cycloalkyl)alkyl, (cycloalkyl)carbonyl, (cycloalkyl)carbonylalkyl, ethylenedioxy, haloalkoxy, haloalkyl, heterocyclyl, heterocyclylalkyl, heterocyclylcarbonyl, heterocyclylcarbonylalkyl, hydroxy, hydroxyalkyl, $NR^AR^B$, $(NR^AR^B)$alkyl, and $(NR^AR^B)$carbonyl;

$R^3$ at each occurance is independently selected from the group consisting of alkenyl, alkoxy, alkoxyalkyl, alkoxycarbonyl, alkyl, alkylcarbonyl, alkylsulfanyl, aryl, arylalkyl, aryloxy, cyano, cyanoalkyl, cycloalkyl, (cycloalkyl)alkyl, halo, haloalkyl, heterocycle, hydroxy, hydroxyalkyl, and nitro;

X is selected from the group consisting of O and S;

m is 0-4; and $R^A$ and $R^B$ are independently selected from the group consisting of hydrogen, alkenyl, alkoxyalkyl, alkyl, alkynyl, alkylcarbonyl, aryl, arylalkyl, cycloalkyl, (cycloalkyl)alkyl, heterocyclyl, heterocyclylalkyl, and hydroxyalkyl.

2. The compound of claim 1 wherein A is pyridinyl.

3. The compound of claim 2 wherein $R^3$ is alkyl; X is O; and m is 1.

4. The compound of claim 3 wherein $R^1$ is selected from the group consisting of hydrogen and alkyl; and $R^2$ is heterocyclylalkyl.

5. A compound of claim 1 selected from the group consisting of

N-benzyl-N'-{(3R)-1-[(6-methylpyridin-3-yl)carbonyl]pyrrolidin-3-yl}urea;
N-{(3R)-1-[(6-methyl-3-pyridinyl)carbonyl]-3-pyrrolidinyl}-1-pyrrolidinecarboxamide;
N-{(3R)-1-[(6-methyl-3-pyridinyl)carbonyl]-3-pyrrolidinyl}-N'-[3-(4-morpholinyl)propyl]urea;
N-[2-(1H-imidazol-4-yl)ethyl]-N'-{(3R)-1-[(6-methyl-3-pyridinyl)carbonyl]-3-pyrrolidinyl}urea;
N-[2-(1H-indol-3-yl)ethyl]-N'-{(3R)-1-[(6-methyl-3-pyridinyl)carbonyl]-3-pyrrolidinyl}urea;
N-ethyl-N'-{(3R)-1-[(6-methyl-3-pyridinyl)carbonyl]-3-pyrrolidinyl}urea;
N-isobutyl-N'-{(3R)-1-[(6-methyl-3-pyridinyl)carbonyl]-3-pyrrolidinyl}urea;
N-(1-methylbutyl)-N'-{(3R)-1-[(6-methyl-3-pyridinyl)carbonyl]-3-pyrrolidinyl}urea;
N-{(3R)-1-[(6-methyl-3-pyridinyl)carbonyl]-3-pyrrolidinyl}-N'-neopentylurea;
N-(3,3-dimethylbutyl)-N'-{(3R)-1-[(6-methyl-3-pyridinyl)carbonyl]-3-pyrrolidinyl}urea;
N-{(3R)-1-[(6-methyl-3-pyridinyl)carbonyl]-3-pyrrolidinyl}-N'-(2,2,2-trifluoroethyl)urea;
N-(2-methoxy-1-methylethyl)-N'-{(3R)-1-[(6-methyl-3-pyridinyl)carbonyl]-3-pyrrolidinyl}urea;
N-(2-ethoxyethyl)-N'-{(3R)-1-[(6-methyl-3-pyridinyl)carbonyl]-3-pyrrolidinyl}urea;
N-{(3R)-1-[(6-methyl-3-pyridinyl)carbonyl]-3-pyrrolidinyl}-N'-(tetrahydro-3-furanylmethyl)urea;
N-(cyanomethyl)-N'-{(3R)-1-[(6-methyl-3-pyridinyl)carbonyl]-3-pyrrolidinyl}urea;
N-{(3R)-1-[(6-methyl-3-pyridinyl)carbonyl]-3-pyrrolidinyl}-N'-2-propynylurea;
N-(cyclopropylmethyl)-N'-{(3R)-1-[(6-methyl-3-pyridinyl)carbonyl]-3-pyrrolidinyl}urea;
N-cyclobutyl-N'-{(3R)-1-[(6-methyl-3-pyridinyl)carbonyl]-3-pyrrolidinyl}urea;
N-cyclohexyl-N'-{(3R)-1-[(6-methyl-3-pyridinyl)carbonyl]-3-pyrrolidinyl}urea;
N-(4-methylcyclohexyl)-N'-{(3R)-1-[(6-methyl-3-pyridinyl)carbonyl]-3-pyrrolidinyl}urea;
N-(cyclohexylmethyl)-N'-{(3R)-1-[(6-methyl-3-pyridinyl)carbonyl]-3-pyrrolidinyl}urea;
N-cycloheptyl-N'-{(3R)-1-[(6-methyl-3-pyridinyl)carbonyl]-3-pyrrolidinyl}urea;
N-[(1S)-1-(hydroxymethyl)-3-methylbutyl]-N'-{(3R)-1-[(6-methyl-3-pyridinyl)carbonyl]-3-pyrrolidinyl}urea;
N-[(1R)-1-(hydroxymethyl)-3-methylbutyl]-N'-{(3R)-1-[(6-methyl-3-pyridinyl)carbonyl]-3-pyrrolidinyl}urea;
N-[(1S)-2-hydroxy-1-phenylethyl]-N'-{(3R)-1-[(6-methyl-3-pyridinyl)carbonyl]-3-pyrrolidinyl}urea;
N-(3-isopropoxypropyl)-N'-{(3R)-1-[(6-methyl-3-pyridinyl)carbonyl]-3-pyrrolidinyl}urea;
N-(2,3-dihydroxypropyl)-N'-{(3R)-1-[(6-methyl-3-pyridinyl)carbonyl]-3-pyrrolidinyl}urea;
N-{(3R)-1-[(6-methyl-3-pyridinyl)carbonyl]-3-pyrrolidinyl}-N'-[2-(2-thienyl)ethyl]urea;
N-[2-(5-methoxy-1H-indol-3-yl)ethyl]-N'-{(3R)-1-[(6-methyl-3-pyridinyl)carbonyl]-3-pyrrolidinyl}urea;
N-(2,4-difluorobenzyl)-N'-{(3R)-1-[(6-methyl-3-pyridinyl)carbonyl]-3-pyrrolidinyl}urea;
N-(3,3-diphenylpropyl)-N'-{(3R)-1-[(6-methyl-3-pyridinyl)carbonyl]-3-pyrrolidinyl}urea;
N-[(1R)-2-hydroxy-1-phenylethyl]-N'-{(3R)-1-[(6-methyl-3-pyridinyl)carbonyl]-3-pyrrolidinyl}urea;
N-{(3R)-1-[(6-methylpyridin-3-yl)carbonyl]pyrrolidin-3-yl}-N'-[(1S)-1-phenylethyl]urea;
N,N-dibutyl-N'-{(3R)-1-[(2-chloro-6-methylpyridin-3-yl)carbonyl]pyrrolidin-3-yl}urea;
N'-{(3R)-1-[(2-chloro-6-methylpyridin-3-yl)carbonyl]pyrrolidin-3-yl}-N-isopropyl-N-(2-methoxyethyl)urea;
N-{(3R)-1-[(2-chloro-6-methylpyridin-3-yl)carbonyl]pyrrolidin-3-yl}-1,3,3-trimethyl-6-azabicyclo[3.2.1]octane-6-carboxamide;
N-{(3R)-1-[(2-chloro-6-methylpyridin-3-yl)carbonyl]pyrrolidin-3-yl}-N'-[(1R)-2-hydroxy-1-phenylethyl]urea;
N-{(3R)-1-[(2-chloro-6-methylpyridin-3-yl)carbonyl]pyrrolidin-3-yl}-N'-(3-ethoxypropyl)urea;
N-{(3R)-1-[(2-chloro-6-methylpyridin-3-yl)carbonyl]pyrrolidin-3-yl}-N'-(3-isopropoxypropyl)urea;
N-{(3R)-1-[(2-chloro-6-methylpyridin-3-yl)carbonyl]pyrrolidin-3-yl}-N'-(3-isobutoxypropyl)urea;
N-{(3R)-1-[(2-chloro-6-methylpyridin-3-yl)carbonyl]pyrrolidin-3-yl}-N'-[3-(methylthio)propyl]urea;
N-benzyl-N'-{(3R)-1-[(2-chloro-6-methylpyridin-3-yl)carbonyl]pyrrolidin-3-yl}-N-ethylurea;
N,N-dibenzyl-N'-{(3R)-1-[(2-chloro-6-methylpyridin-3-yl)carbonyl]pyrrolidin-3-yl}urea;
N'-{(3R)-1-[(2-chloro-6-methylpyridin-3-yl)carbonyl]pyrrolidin-3-yl}-N-methyl-N-(2-phenylethyl)urea;
N'-{(3R)-1-[(2-chloro-6-methylpyridin-3-yl)carbonyl]pyrrolidin-3-yl}-N-[2-(3,4-dimethoxyphenyl)ethyl]-N-methylurea;
4-benzyl-N-{(3R)-1-[(2-chloro-6-methylpyridin-3-yl)carbonyl]pyrrolidin-3-yl}piperidine-1-carboxamide;
N-{(3R)-1-[(2-chloro-6-methylpyridin-3-yl)carbonyl]pyrrolidin-3-yl}-4-(2-oxo-2,3-dihydro-1H-benzimidazol-1-yl)piperidine-1-carboxamide;
N-{(3R)-1-[(2-chloro-6-methylpyridin-3-yl)carbonyl]pyrrolidin-3-yl}-4-phenylpiperazine-1-carboxamide;
N-[2-(diethylamino)ethyl]-N-methyl-N'-{(3R)-1-[(6-methylpyridin-3-yl)carbonyl]pyrrolidin-3-yl}urea;
N-benzyl-N-ethyl-N'-{(3R)-1-[(6-methylpyridin-3-yl)carbonyl]pyrrolidin-3-yl}urea;
N-benzyl-N-isopropyl-N'-{(3R)-1-[(6-methylpyridin-3-yl)carbonyl]pyrrolidin-3-yl}urea;
N-benzyl-N-butyl-N'-{(3R)-1-[(6-methylpyridin-3-yl)carbonyl]pyrrolidin-3-yl}urea;
N,N-dibenzyl-N'-{(3R)-1-[(6-methylpyridin-3-yl)carbonyl]pyrrolidin-3-yl}urea;
N-benzyl-N'-{(3R)-1-[(6-methylpyridin-3-yl)carbonyl]pyrrolidin-3-yl}-N-(2-phenylethyl)urea;
$N^3,N^3$-diethyl-$N^1$-{(3R)-1-[(6-methylpyridin-3-yl)carbonyl]pyrrolidin-3-yl}piperidine-1,3-dicarboxamide;
N-{(3R)-1-[(6-methylpyridin-3-yl)carbonyl]pyrrolidin-3-yl}-4-(2-oxo-2,3-dihydro-1H-benzimidazol-1-yl)piperidine-1-carboxamide;
4-ethyl-N-{(3R)-1-[(6-methylpyridin-3-yl)carbonyl]pyrrolidin-3-yl}piperazine-1-carboxamide;
4-benzyl-N-{(3R)-1-[(6-methylpyridin-3-yl)carbonyl]pyrrolidin-3-yl}piperazine-1-carboxamide;
N-methyl-N'-{(3R)-1-[(6-methylpyridin-3-yl)carbonyl]pyrrolidin-3-yl}-N-propylurea;
N-isobutyl-N-methyl-N'-{(3R)-1-[(6-methylpyridin-3-yl)carbonyl]pyrrolidin-3-yl}urea;
N-methyl-N-(3-methylbutyl)-N'-{(3R)-1-[(6-methylpyridin-3-yl)carbonyl]pyrrolidin-3-yl}urea;
N-methyl-N'-{(3R)-1-[(6-methylpyridin-3-yl)carbonyl]pyrrolidin-3-yl}-N-prop-2-ynylurea;

N-ethyl-N'-{(3R)-1-[(6-methylpyridin-3-yl)carbonyl]pyrrolidin-3-yl}-N-propylurea;
N-isopropyl-N'-{(3R)-1-[(6-methylpyridin-3-yl)carbonyl]pyrrolidin-3-yl}-N-propylurea;
N-(sec-butyl)-N'-{(3R)-1-[(6-methylpyridin-3-yl)carbonyl]pyrrolidin-3-yl}-N-propylurea;
N,N-dibutyl-N'-{(3R)-1-[(6-methylpyridin-3-yl)carbonyl]pyrrolidin-3-yl}urea;
N-(2-cyanoethyl)-N-cyclopropyl-N'-{(3R)-1-[(6-methylpyridin-3-yl)carbonyl]pyrrolidin-3-yl}urea;
2-ethyl-N-{(3R)-1-[(6-methylpyridin-3-yl)carbonyl]pyrrolidin-3-yl}piperidine-1-carboxamide;
N-{(3R)-1-[(6-methylpyridin-3-yl)carbonyl]pyrrolidin-3-yl}-4-propylpiperidine-1-carboxamide;
N-{(3R)-1-[(6-methylpyridin-3-yl)carbonyl]pyrrolidin-3-yl}azepane-1-carboxamide;
N-ethyl-N-(2-methoxyethyl)-N'-{(3R)-1-[(6-methylpyridin-3-yl)carbonyl]pyrrolidin-3-yl}urea;
N-(2-methoxyethyl)-N'-{(3R)-1-[(6-methylpyridin-3-yl)carbonyl]pyrrolidin-3-yl}-N-propylurea;
N,N-bis(2-methoxyethyl)-N'-{(3R)-1-[(6-methylpyridin-3-yl)carbonyl]pyrrolidin-3-yl}urea;
1,3,3-trimethyl-N-{(3R)-1-[(6-methylpyridin-3-yl)carbonyl]pyrrolidin-3-yl}-6-azabicyclo[3.2.1]octane-6-carboxamide;
N-methyl-N'-{(3R)-1-[(6-methylpyridin-3-yl)carbonyl]pyrrolidin-3-yl}-N-(2-phenylethyl)urea;
4-sec-butyl-N-{(3R)-1-[(6-methylpyridin-3-yl)carbonyl]pyrrolidin-3-yl}piperazine-1-carboxamide;
4-(2-ethoxyethyl)-N-{(3R)-1-[(6-methylpyridin-3-yl)carbonyl]pyrrolidin-3-yl}piperazine-1-carboxamide;
4-cyclohexyl-N-{(3R)-1-[(6-methylpyridin-3-yl)carbonyl]pyrrolidin-3-yl}piperazine-1-carboxamide;
N-{(3R)-1-[(6-methylpyridin-3-yl)carbonyl]pyrrolidin-3-yl}-4-(2-thien-2-ylethyl)piperazine-1-carboxamide;
N-{(3R)-1-[(6-methylpyridin-3-yl)carbonyl]pyrrolidin-3-yl}-4-(2-oxo-2-piperidin-1-ylethyl)piperazine-1-carboxamide;
4-(cyclohexylcarbonyl)-N-{(3R)-1-[(6-methylpyridin-3-yl)carbonyl]pyrrolidin-3-yl}piperazine-1-carboxamide;
N-benzyl-N-(2-hydroxyethyl)-N'-{(3R)-1-[(6-methylpyridin-3-yl)carbonyl]pyrrolidin-3-yl}urea;
N-(2-hydroxy-2-phenylethyl)-N-methyl-N'-{1-[(6-methylpyridin-3-yl)carbonyl]pyrrolidin-3-yl}urea;
N-methyl-N'-{(3R)-1-[(6-methylpyridin-3-yl)carbonyl]pyrrolidin-3-yl}-N-(2-pyridin-2-ylethyl)urea;
4-hydroxy-N-{(3R)-1-[(6-methylpyridin-3-yl)carbonyl]pyrrolidin-3-yl}piperidine-1-carboxamide;
$N^1$-{(3R)-1-[(6-methylpyridin-3-yl)carbonyl]pyrrolidin-3-yl}piperidine-1,4-dicarboxamide;
N-{(3R)-1-[(6-methylpyridin-3-yl)carbonyl]pyrrolidin-3-yl}-1,4-dioxa-8-azaspiro[4.5]decane-8-carboxamide;
2,6-dimethyl-N-{(3R)-1-[(6-methylpyridin-3-yl)carbonyl]pyrrolidin-3-yl}morpholine-4-carboxamide;
N-{(3R)-1-[(6-methylpyridin-3-yl)carbonyl]pyrrolidin-3-yl}-4-phenylpiperazine-1-carboxamide;
N-{(3R)-1-[(6-methylpyridin-3-yl)carbonyl]pyrrolidin-3-yl}-4-pyridin-2-ylpiperazine-1-carboxamide;
4-(2-fluorophenyl)-N-{(3R)-1-[(6-methylpyridin-3-yl)carbonyl]pyrrolidin-3-yl}piperazine-1-carboxamide;
4-(4-fluorophenyl)-N-{(3R)-1-[(6-methylpyridin-3-yl)carbonyl]pyrrolidin-3-yl}piperazine-1-carboxamide;
4-(2-methoxyphenyl)-N-{(3R)-1-[(6-methylpyridin-3-yl)carbonyl]pyrrolidin-3-yl}piperazine-1-carboxamide;
4-methyl-N-{(3R)-1-[(6-methylpyridin-3-yl)carbonyl]pyrrolidin-3-yl}-1,4-diazepane-1-carboxamide;
ethyl {4-[({(3R)-1-[(6-methylpyridin-3-yl)carbonyl]pyrrolidin-3-yl}amino)carbonyl]piperazin-1-yl}acetate;
N-{(3R)-1-[(6-methylpyridin-3-yl)carbonyl]pyrrolidin-3-yl}-4-(4-nitrophenyl)piperazine-1-carboxamide; and
3-(methoxymethyl)-N-{(3R)-1-[(6-methylpyridin-3-yl)carbonyl]pyrrolidin-3-yl}piperidine-1-carboxamide.

6. A pharmaceutical composition comprising a compound of claim 1 or a therapeutically acceptable salt thereof, in combination with a therapeutically acceptable carrier.

* * * * *